US012566186B2

(12) United States Patent
Grabert et al.

(10) Patent No.: US 12,566,186 B2
(45) Date of Patent: *Mar. 3, 2026

(54) ASSAYS FOR DETECTING THE PRESENCE OR AMOUNT OF AN ANTI-DRUG ANTIBODY

(71) Applicant: GENZYME CORPORATION, Cambridge, MA (US)

(72) Inventors: Ryan Grabert, Cambridge, MA (US); Susan Richards, Cambridge, MA (US); Valerie Theobald, Cambridge, MA (US); Yuanxin Xu, Cambridge, MA (US); Jad Zoghbi, Cambridge, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/428,535

(22) Filed: Jan. 31, 2024

(65) Prior Publication Data

US 2024/0288454 A1     Aug. 29, 2024

Related U.S. Application Data

(60) Continuation of application No. 17/534,012, filed on Nov. 23, 2021, now Pat. No. 11,927,596, which is a division of application No. 15/671,663, filed on Aug. 8, 2017, now Pat. No. 11,215,623, which is a division of application No. 14/619,422, filed on Feb. 11, 2015, now Pat. No. 9,759,732.

(60) Provisional application No. 61/938,556, filed on Feb. 11, 2014.

(51) Int. Cl.
| | |
|---|---|
| *G01N 33/53* | (2006.01) |
| *G01N 33/539* | (2006.01) |
| *G01N 33/68* | (2006.01) |
| *G01N 33/94* | (2006.01) |

(52) U.S. Cl.
CPC ......... *G01N 33/94* (2013.01); *G01N 33/5306* (2013.01); *G01N 33/539* (2013.01); *G01N 33/6854* (2013.01); *G01N 2430/00* (2013.01)

(58) Field of Classification Search
None
See application file for complete search history.

(56) References Cited

U.S. PATENT DOCUMENTS

| | | | |
|---|---|---|---|
| 5,187,065 A | 2/1993 | Schutzer et al. | |
| 9,759,732 B2 | 9/2017 | Grabert et al. | |
| 11,215,623 B2 | 1/2022 | Grabert et al. | |
| 11,927,596 B2 * | 3/2024 | Grabert | G01N 33/94 |
| 2010/0120170 A1 | 5/2010 | Dodds et al. | |
| 2015/0226758 A1 | 8/2015 | Grabert et al. | |
| 2016/0313322 A1 * | 10/2016 | Stubenrauch | A61P 13/12 |
| 2018/0088140 A1 | 3/2018 | Grabert et al. | |
| 2022/0187327 A1 | 6/2022 | Grabert et al. | |

FOREIGN PATENT DOCUMENTS

| | | |
|---|---|---|
| EP | 3105592 A1 | 12/2016 |
| EP | 3422001 A1 | 1/2019 |
| EP | 3667321 A1 | 6/2020 |
| JP | 2010-078374 A | 4/2010 |
| WO | WO 1990/006515 A1 | 6/1990 |
| WO | WO 2007/101661 A1 | 9/2007 |
| WO | WO 2008/137885 A1 | 11/2008 |
| WO | WO 2009/091240 A1 | 7/2009 |
| WO | WO 2012154253 A1 | 11/2012 |
| WO | WO 2013/132000 A1 | 9/2013 |
| WO | WO 2015123315 A1 | 8/2015 |

OTHER PUBLICATIONS

Barbosa et al. (2012) "Addressing drug effects on cut point determination for an anti-drug antibody assay," Journal of Immunological Methods. 384:152-156.

Bartelds et al. (2011) "Development of Antidrug Antibodies Against Adalimumab and Association With Disease Activity and Treatment Failure During Long-term Follow-up," JAMA. 305(14):1460-1468.

Bourdage et al. (2007) "An Affinity Capture Elution (ACE) assay for detection of anti-drug antibody to monoclonal antibody therapeutics in the presence of high levels of drug," Journal of Immunological Methods. 327(1-2):10-17.

Dai et al. (2014) "Development of a method that eliminates false-positive results due to nerve growth factor interference in the assessment of fulranumab immunogenicity," AAPS J. 16(3):464-477.

De Carvalho et al. (Oct. 30, 2012) "A Simple immune complex dissociation ELISA for leishmaniasis: Standardization of the assay in experimental models and preliminary results," Acta Tropica. 125:128-136.

Extended European Search Report received for European Application No. 18188141.8, mailed on Sep. 10, 2018.

Extended European Search Report received for European Patent Application No. 20154994.6, mailed on Mar. 27, 2020.

International Preliminary Report on Patentability corresponding to International Patent Application No. PCT/US2015/015442, dated Aug. 16, 2016.

International Search Report with Written Opinion corresponding to International Patent Application No. PCT/US2015/015442, mailed May 26, 2015.

Meso Scale Diagnostics, LLC. (2013) "MSD Technology Platform," Accessible on the Internet at URL: https://www.mesoscale.com/-/media/files/brochures/techbrochure.pdf, 16 pgs. [Last Accessed Jan. 29, 2016].

(Continued)

*Primary Examiner* — Gary Counts
(74) *Attorney, Agent, or Firm* — LATHROP GPM LLP; James H. Velema, Esq.; Judith L. Stone-Hulslander, Esq.

(57)     ABSTRACT

Methods and kits for detecting antibodies (e.g., anti-drug antibodies). Such methods and kits permit the detection of, for example, anti-drug antibodies in human body fluids, such as blood, plasma and serum.

19 Claims, 10 Drawing Sheets

(56)          References Cited

OTHER PUBLICATIONS

Mire-Sluis et al. (2004) "Recommendations for the design and optimization of immunoassays used in the detection of host antibodies against biotechnology products," Journal of Immunological Methods. 289(1-2):1-16.

MSD Meso Scale Discovery®, "MSD Technology Platform", 2013, Retrieved from url: <https://www.mesoscale.com/~/media/files/brochures/techbrochure.pdf>.

Murayama et al. (2006) "A sensitive radioimmunoassay of insulin autoantibody: Reduction of non-specific binding of [<125>1] insulin," Journal of Autoimmunity. 26(2):127-132.

Ohlson et al. (1985) "Detection of Circulating Immune Complexes by PEG Precipitation Combined with ELISA," J. Immunol. Methods. 77:87-93.

Ronnelid (2003) "Immune complexes from SLE sera induce ID 0 production from normal peripheral blood mononuclear cells by an FcgRII dependent mechanism: implications for a possible vicious cycle maintaining B cell hyperactivity in SLE," Ann. Rheum. Dis. 62:37-42.

Rote List® 2008, "Hypophysen-, Hypothalamushormone, andere regulatorische Peptide u. ihre Hemmstoffe", 2008, Chapter 50, 20 pages.

Shankar et al. (2008) "Recommendations for the validation of immunoassays used for detection of host antibodies against biotechnology products," Journal of Pharmaceutical and Biomedical Analysis. 48(5):1267-1281.

Sickert et al., "Improvement of drug tolerance in immunogenicity testing by acid treatment on Biacore", Journal of Immunological Methods, May 20, 2008, 334(1-2): 29-36.

Wang et al., "Hematologic Disorders Diagnosis and Therapy", Diagnosis and Treatment of Hematonosis—Diagrammatic Approach, Dec. 31, 2004, pp. 30-31.

Zhang et al., "Clinical Transfusion", Shanghai Science and Technology Press, Dec. 31, 2000, pp. 92-94.

* cited by examiner

ASSAYS FOR DETECTING THE PRESENCE OR AMOUNT OF AN ANTI-DRUG ANTIBODY

CROSS-REFERENCE TO RELATED APPLICATIONS

This application is a continuation of U.S. patent application Ser. No. 17/534,012, filed Nov. 23, 2021, now U.S. Pat. No. 11,927,596, which is a division of U.S. patent application Ser. No. 15/671,663, filed Aug. 8, 2017, now U.S. Pat. No. 11,215,623, which is a division of U.S. patent application Ser. No. 14/619,422, filed Feb. 11, 2015, now U.S. Pat. No. 9,759,732, which claims the benefit of U.S. Provisional Patent Application Ser. No. 61/938,556, filed Feb. 11, 2014, the entire contents of which are hereby incorporated by reference.

TECHNICAL FIELD

This invention relates to methods and kits for detecting the presence of anti-drug antibodies in a sample, and more particularly to methods and kits for detecting anti-drug antibodies in the presence of a drug in the sample.

BACKGROUND

The introduction of biotherapeutics (e.g., biologic agents such as proteins, peptides, nucleotides, etc.) has given a major boost to the treatment of diseases such as inflammatory bowel disease, ankylosing spondylitis, multiple sclerosis and rheumatoid arthritis. In many cases these biological agents have proven very successful in clinical practice. Biologic agents, including therapeutic antibodies, are known to have immunogenic potential, and administration of therapeutic proteins to a patient can induce immune response leading to the formation of anti-drug antibodies ("ADAs"). Such ADAs may reduce the effectiveness of the therapeutic protein. For example, they may bind to or/and neutralize the therapeutic protein, resulting in changes of drug pharmacokinetics or pharmacodynamics that alters drug efficacy. ADAs may cause serious side effects, including allergic reactions, cross-reactivity against endogenous proteins by neutralizing antibodies (NAbs), and complement activation. The production of ADAs have been described for several monoclonal antibodies available for the treatment of rheumatoid arthritis (adalimumab and infliximab), Crohn's disease (infliximab), multiple sclerosis (natalizumab and alemtuzumab) and plaque psoriasis (adalimumab). In some patients, the clinical benefits provided by such therapeutic proteins diminishes over time due to the formation of ADAs. Immunogenicity_risk assessment is critical to understand frequency and severity for drug induced ADA. NAb cross-reactive to endogenous protein causing depletion syndrome has been reported (erythropoietin).

With an increasing number of therapeutic proteins approved for clinical use, the immunogenicity of such products has become informative to clinicians, manufacturers and regulatory agencies. It is well-established that certain substances will affect the detection or quantitation of an analyte in immunoassays (or ligand binding assays). These interference factors including but not limited to circulating drugs negatively impact assay specificity, accuracy, and sensitivity. "Drug interference" that reduce ADA assay "drug tolerance" is regarded as a major technical challenge for immunogenicity assessment to monitor ADA as part of patient's monitoring for drug clinical safety and efficacy.

Although the above approaches demonstrated some improvement in drug tolerance, sensitivity and relative accuracy is not maintained in comparison to no-drug ADA detection therefore risking false negative and under-reporting ADA incidence and titers in treated patients. Despite industry regulatory guidance documents and white papers recommending sensitivity between 250 and 500 ng/mL [Shankar G, Devanarayan V, Amaravadi L et al.: Recommendations for the validation of immunoassays used for detection of host antibodies against biotechnology products. Journal of Pharmaceutical and Biomedical Analysis 48 (5), 1267-1281 (2008); Mire-Sluis A R, Barrett Y C, Devanarayan V et al.: Recommendations for the design and optimization of immunoassays used in the detection of host antibodies against biotechnology products. Journal of Immunological Methods 289 (1-2), 1-16 (2004)], drug tolerance is sometimes evaluated without any acceptance criteria and clinical protocols are then written instructing long wash-out periods before antibody measurement to allow for drug clearance and the avoidance of false negative results due to drug interference. This approach is not desired due to risks in missing ADA assessment in early time points especially in the case with a long half-life drug and/or multi-dosing regimen and the wash out period approach is not feasible. Some non-ligand binding based methods such as mass spectrometry has been evaluated for PK in the presence of ADA interference, the expected assay sensitivity has not been acceptable and enrichment of analyte is needed which is ligand binding based which poses the similar challenges.

A variety of assay formats have been used with success to detect ADAs, including ELISA (direct, indirect and bridging), radioimmunoassays, electrochemiluminescence, and surface plasmon resonance. The development of such assays, however, is often complicated by interference caused by the presence of the drug. The challenge of analytical interferences in ligand binding assays has long been recognized. With the advent of long-lived monoclonal antibody therapies, the need for specific techniques to detect ADA in the presence of drug is of particular concern. The most widely adopted approaches in use currently still have limitations of timing, sensitivity or accuracy. Thus, there is a need in the art for methods and kits to more accurately and reproducibly detect the presence of ADA in samples, such as biological samples.

SUMMARY

The present invention is based, at least in part, on the discovery of a novel assay method that is effective for reducing or eliminating the problems caused by interference by drug or target in ADA detection. In particular, the present invention is based on the development of a novel ADA assay comprising the following exemplary steps. First, excess drug material is added to the samples containing potential ADAs (both free ADA and ADA/drug complex) to bind all remaining free ADAs, forming drug/ADA complexes. Second, these complexes are precipitated using polyethylene glycol. Third, after a series of washes to remove serum protein and immunoglobulin, the final precipitate (drug/ADA complexes) is reconstituted with a solution to dissociate the complexes and then coated on a large surface (under conditions to keep drug and ADA apart) or substrate (e.g., a high bind carbon plate with high coating capacity) for a time sufficient to allow coating of all dissociated free drugs and free ADAs. Fourth, specific detection of the total ADA levels is then performed using labeled drug. Accordingly, the present invention relates to methods, compositions and kits for determining the presence or amount of an ADA in a sample (e.g., a biologic sample).

In one embodiment, the final precipitate (drug/ADA complexes) is reconstituted with an acid solution to dissociate the complexes and then coated on a large surface (under acidic conditions to keep drug and ADA apart) or substrate (e.g., a high bind carbon plate with high coating capacity) for a time sufficient to allow coating of all dissociated free drugs and free ADAs. The acidic environment prevents the complexes from reforming while being immobilized onto the substrate surface. When an acid solution is used to dissociate the complexes, the assay can be referred to as a PandA (PEG and Acid) assay.

In another embodiment, the final precipitate (drug/ADA complexes) is reconstituted with a basic solution to dissociate the complexes and then coated on a large surface (under basic conditions to keep drug and ADA apart) or substrate (e.g., a high bind carbon plate with high coating capacity) for a time sufficient to allow coating of all dissociated free drugs and free ADAs. The basic environment prevents the complexes from reforming while being immobilized onto the substrate surface.

The selection of an acidic or basic solution will depend on the parameters of the drug (e.g., the biologic drug), such as pI, or the presence of certain conjugating bonds, and the selection will have minimal effect on the integrity and structure of the drug. In some embodiments, the incubation step following the initial acid or base addition can be carried out at 22° C., 23° C., 25° C., 27° C., 30° C., 32° C., 35° C., 37° C., 39° C. or higher.

In some embodiments, following the final precipitation step, each sample can be further diluted to a final sample dilution of, e.g., 1:20, 1:25, 1:30, 1:40, 1:50, or 1:60.

In one aspect, the disclosure provides a method for determining the presence or absence of an ADA in a sample, the method comprising contacting the sample with an excess amount of drug to which the ADA binds to form drug/ADA complexes, contacting the drug/ADA complexes with polyethylene glycol (PEG), to form a precipitate comprising drug/ADA complexes, contacting the precipitate with a solution to dissociating the drug/ADA complexes, immobilizing the dissociated ADAs on a surface and/or substrate, and determining the presence of or amount of said ADA. In a further aspect, the determining step comprises contacting the immobilized ADA with drug conjugated with a detectable label, and determining the presence of or amount of said detectable label, to thereby determine the presence or amount (titer) of ADA in the sample.

In some embodiments, the method for determining the presence or absence of an ADA in a sample further comprises before, after or part of the determining step, determining the amount of ADA in the sample.

In some embodiments, the method for determining the presence or absence of an ADA in a biological sample further comprises, after the immobilizing step, treating (e.g., washing) the support to remove unbound drug.

In other embodiments, the method for determining the presence or absence of an ADA in a biological sample further comprises, after contacting the sample with PEG, washing the precipitate.

In still other embodiments, the method further comprises immobilizing the drug on the substrate before, after or during the step of immobilizing the ADA on the substrate.

In another aspect, the disclosure provides a method for reducing interference in a drug assay (e.g., a drug PK assay, a drug quantitation assay, or a drug potency assay) due to the presence of an ADA in a sample, the method comprising contacting the sample with an excess amount of ADA to saturate free drug and form drug/ADA complexes, contacting the drug/ADA complexes with polyethylene glycol (PEG), to thereby form a precipitate comprising drug/ADA complexes, contacting the precipitate with a solution to dissociating the drug/ADA complexes, immobilizing the dissociated drug on a substrate under acidic conditions, and performing the drug assay using specific detection reagent for drug, to thereby reduce interference from the ADA. The drug assay can be, for example, a drug quantitation assay, a drug PK assay or a drug potency assay.

In some embodiments, the method for reducing interference in a drug assay due to the presence of an ADA further comprises determining the presence or absence of, or the amount of the drug in the sample using an anti-idiotype antibody labeled with a detectable label.

In some embodiments, the methods disclosed herein further comprise diluting the sample before it is contacted with an excess amount of drug. For example, the sample is diluted 1:2, 1:5, 1:10, 1:20 fold before it is contacted with an excess amount of drug.

In other embodiments, the sample comprises a biological sample, wherein the biological sample comprises a material selected from the group consisting of body fluids, mucus secretions, saliva, blood, whole blood, plasma or serum. In some embodiments, the sample comprises a drug.

In still other embodiments, the drug comprises an antibody or fragment thereof, a dual affinity antibody, diabody, multiple domain biologics (such as antibody drug conjugate), a nucleic acid (siRNA, antisense oligonucleotide, gene therapy drugs), a peptide or a polypeptide (native or modified), a peptidomimetic, a carbohydrate, a lipid, or an organic or inorganic small molecule compound, or any combinations thereof. In some embodiments, the drug comprises a therapeutic antibody, a protein therapeutic, an enzyme, an engineered binding protein, an engineered antibody-like protein, a fusion protein, a scaffold protein, or any combinations thereof. When the drug comprises an antibody or fragment thereof, the antibody may be a murine, human, humanized or chimeric antibody. In some embodiments, the drug is a drug modified to exhibit less immunogenicity as compared to the same drug in unmodified form (i.e., the drug has been modified to be less immunogenic).

In some embodiments, the substrate comprises a carbon surface, glass surface, silica surface, metal surface, a polymeric material, a surface containing a metallic or chemical coating, a membrane, a bead (e.g., a micro-bead), a porous polymer matrix, a substrate comprising cellulosic fibers, or any combinations thereof. The substrate can comprise a polymeric material, wherein the polymeric material is selected from the group consisting of polystyrene, polyvinyl chloride, polypropylene, polyethylene, polyamide, and polycarbonate.

In some embodiments, the substrate comprises a porous carbon surface. In one embodiment, the substrate is a high bind carbon plate.

In some embodiments, the substrate comprises a large surface with high coating capacity. A substrate comprising a large surface with high coating capacity includes, for example, a high bind carbon plate (e.g., a MSD MESO SCALE DISCOVERY®, Rockville Maryland).

In some embodiments, the methods provided comprise contacting drug/ADA complexes with polyethylene glycol (PEG) to form a precipitate comprising drug/ADA complexes. The PEG comprises at least one PEG compound having a molecular weight between 1,000 and 40,000 daltons, including, for example at least one PEG compound selected from the group consisting of PEG1000, PEG1450, PEG3000, PEG6000, PEG8000, PEG10000, PEG14000, PEG15000, PEG20000, PEG250000, PEG30000, PEG35000, and PEG40000.

In one or more embodiments, the sample is contacted with PEG at a concentration of between about 0.1% and about 10.0%, about 0.2% and about 7.0%, between about 0.5% and about 6.0%, between about 0.5% and about 5.0%, between about 1.5% and about 5.5%, between about 2.0% and about 5.0%, between about 3.0% and about 4.5%, between about 3.5% and about 4.0%, between about 1.0% and about 2.5%, between about 1.2% and about 1.5%, or about 0.1%, 0.2%, 0.5%, 1.0%, 1.2%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5% or about 10.0% PEG.

In other embodiments, the methods comprise contacting a precipitate comprising an ADA and/or ADA/drug complex with an acid solution. The acid solution can comprise an organic acid, an inorganic acid, or a mixture thereof. In some aspects, the acid solution comprises an acid selected from the group consisting of citric acid, isocitric acid, glutamic acid, acetic acid, lactic acid, formic acid, oxalic acid, uric acid, trifluoroacetic acid, benzene sulfonic acid, aminomethanesulfonic acid, camphor-10-sulfonic acid, chloroacetic acid, bromoacetic acid, iodoacetic acid, propanoic acid, butanoic acid, glyceric acid, succinic acid, malic acid, aspartic acid, hydrochloric acid, nitric acid, phosphoric acid, sulfuric acid, boric acid, hydrofluoric acid, hydrobromic acid and any combinations thereof. In an exemplary embodiment, the acid solution comprises acetic acid. For methods comprising contacting a precipitate comprising an ADA and/or ADA/drug complex with an acid solution, the precipitate is contacted with an acid at a concentration of between about 0.1M to about 5M.

In other embodiments, the methods comprise contacting a precipitate comprising an ADA and/or ADA/drug complex with a base solution. The base solution can comprise an organic base, an inorganic base, or a mixture thereof. In some aspects, the base solution comprises a base selected from the group consisting of urea, sodium hydroxide, rubidium hydroxide, cesium hydroxide, calcium hydroxide, strontium hydroxide, barium hydroxide, zinc hydroxide, lithium hydroxide, acetone, methylamine, and ammonia. For methods that include contacting a precipitate comprising an ADA and/or ADA/drug complex with a basic solution, the precipitate is contacted with a base at a concentration of between about 0.1 M to about 1 M.

In some aspects, the disclosure provides antibodies, anti-drug antibodies and drug labeled with (i.e., conjugated to) a detectable label. The detectable label comprises a label selected from the group consisting of a hapten, radioactive isotope, an enzyme, a fluorescent label, a chemiluminescent label, and electro-chemiluminescent label, a first member of a binding pair, and a substrate for an enzymatic detection reaction. In one embodiment, the detectable label comprises an electrohemiluminescent label comprising a SULFO-TAG® label.

In some embodiments, the detectable label comprises a fluorophore, wherein the fluorophore is selected from the group consisting green fluorescent protein, blue fluorescent protein, red fluorescent protein, fluorescein, fluorescein 5-isothiocyanate (FITC), cyanine dyes (Cy3, Cy3.5, Cy5, Cy5.5, Cy7), Bodipy dyes (Invitrogen) and/or Alexa Fluor dyes (Invitrogen), dansyl, Dansyl Chloride (DNS-C1), 5-(io-doacetamida) fluorescein (5-IAF, 6-acryloyl-2-dimethylami-nonaphthalene (acrylodan), 7-nitrobenzo-2-oxa-1,3,-diazol- 4-yl chloride (NBD-C1), ethidium bromide, Lucifer Yellow, rhodamine dyes (5-carboxyrhodamine 6G hydrochloride, Lissamine rhodamine B sulfonyl chloride, rhodamine-B-isothiocyanate (RITC (rhodamine-B-isothiocyanate), rhod-amine 800); tetramethylrhodamine 5-(and 6-) isothiocyanate (TRITC)), Texas Red™, sulfonyl chloride, naphthalamine sulfonic acids including but not limited to 1-anilinonaph-thalene-8-sulfonic acid (ANS) and 6-(p-toluidinyl) naphtha-len-e-2-sulfonic acid (TNS), Anthroyl fatty acid, DPH, Pari-naric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, Naphtyl Styryl, 3,3'dipropylthiadicarbocyanine (diS-C3-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, IR-125, Thiazole Orange, Azure B, Nile Blue, Al Phthalocyanine, Oxaxine 1, 4', 6-diamidino-2-phenylindole. (DAPI), Hoechst 33342, TOTO, Acridine Orange, Ethidium Homodimer, N (ethoxycarbonylmethyl)-6-methoxyquinolinium (MQAE), Fura-2, Calcium Green, Carboxy SNARF-6, BAPTA, coumarin, phytofiuors and Coronene.

In some embodiments, the detectable label comprises an enzyme that catalyzes a color change reaction, including, an enzyme selected from the group consisting of alkaline phosphatase, beta-galactosidase, horse radish peroxidase, urease and beta-lactamase and glucose oxidase.

In some embodiments, the detectable label comprises a first member of a binding pair or a second member of a binding pair, wherein the binding pair is selected from the group consisting of biotin/streptavidin, biotin/avidin, biotin/neutravidin, biotin/captavidin, epitope/antibody, protein A/immunoglobulin, protein G/immunoglobulin, protein L/immunoglobulin, GST/glutathione, His-tag/Nickel, anti-gen/antibody, FLAG/M1 antibody, maltose binding protein/maltose, calmodulin binding protein/calmodulin, enzyme-enzyme substrate, and receptor-ligand binding pairs.

In some embodiments, the detectable label comprises a first member of a binding pair; and the second member of the binding pair is conjugated to an enzyme, an antibody epitope, an antigen, a fluorophore, a radioisotope, a nan-oparticle, a member of a second binding pair, and a metal chelate.

In other embodiments, the detectable label comprises a first member of a binding pair, wherein the first member of the binding pair is biotin and the second member of the binding pair is selected from the group consisting of streptavidin, avidin, neutravidin and capravidin, and the second member of the binding pair conjugated to an enzyme.

The methods provided herein can be performed on either a manual or automated instrument platform, depending on the number of samples to be tested.

"Anti-drug antibodies" or "ADAs" are antibodies that bind specifically to any region of a drug. For example, an anti-drug antibody may be an antibody or fragment thereof, which may be directed against any region of a drug antibody, e.g., the variable domain, the constant domains, or the glycostructure of the antibody). Such anti-drug antibodies may occur during drug therapy as an immunogenic reaction of a patient. An ADA may be one of any human immuno-globulin isotype (e.g., IgM, IgE, IgA, IgG, IgD) or IgG subclass (IgG1, 2, 3, and 4). ADAs include ADAs from any animal source, including, for example, human or non-human animal (e.g. veterinary) sources.

For the purpose of the present specification, the term "NAb" or "neutralizing antibody" refers to an antibody that binds to an endogenously produced molecule, e.g., an antibody, nucleic acid, peptide, polypeptide, peptidomimetic, carbohydrate or lipid. For example, a NAb may be an endogenously produced protein, such as, for example, erythropoietin or insulin. The NAb may or may not reduce (e.g., neutralizes) at least one biological activity of the endogenously produced molecule.

For instance, in some aspects, the disclosure provides a method for determining the presence or absence of NAb in a sample, the method comprising contacting the sample with an excess amount of antigen to which the NAb binds to form an antigen/Nab complexes, contacting the antigen/NAb complexes with polyethylene glycol (PEG), to form a precipitate comprising antigen/NAb complexes, contacting the precipitate with a solution to dissociate the antigen/NAb complexes, immobilizing the dissociated NAbs on a surface and/or substrate, and determining the presence of or amount of said NAb. In a further aspect, the determining step comprises contacting the immobilized NAb with of an antigen to which the Nab binds conjugated with a detectable label, and determining the presence of or amount of said detectable label, to thereby determine the presence or amount (titer) of NAb in the sample.

In the context of the invention, the term "patient" refers to any subject, preferably a mammal, and more preferably a human, with a disease or suspected of having a disease. The term "subject," as used herein, refers to any animal (e.g., a human or non-human animal subject). In some instances, the subject is a mammal. In some instances, the term "subject", as used herein, refers to a human (e.g., a man, a woman, or a child). In some instances, the term "subject", as used herein, refers to laboratory animal of an animal model study.

As used herein, the term "biological sample" or "sample" refers to a sample obtained or derived from a patient which comprises patient derived immunoglobulin and may therefore be referred to as an immunoglobulin sample. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, and an immunoglobulin enriched fraction derived from one or more of these tissues. In some embodiments the sample is, or comprises blood serum or is an immunoglobulin enriched fraction derived from blood serum or blood. The sample is, or can be derived (obtained) from, a bodily fluid or body tissue. In some embodiments, the sample is obtained from a subject who has been exposed to the drug, such as repeatedly exposed to the same drug. In other embodiments, the sample is obtained from a subject who has not recently been exposed to the drug, or obtained from the subject prior to the planned administration of the drug.

The term "substrate", as used herein refers to any material or macromolecular complex to which an ADA or drug material (e.g., an antibody, nucleic acid, peptide, polypeptide, peptidomimetic, carbohydrate, lipid, or an organic or inorganic small molecule compound) may bind. The composition and/or surface of the substrate should allow for binding of an ADA or drug material under acidic conditions (or basic conditions) that allow for dissociation of the ADA/drug complexes. In some embodiments, these substrates have a high loading capacity, which improves sensitivity, thus allowing for detection of ADAs and/or drug materials present in relatively low concentrations. Examples of commonly used substrates include, but are not limited to, carbon surfaces (e.g. a porous or high bind carbon plate), glass surfaces, silica surfaces, plastic surfaces, metal surfaces, surfaces containing a metallic or chemical coating, membranes (e.g., nylon, polysulfone, silica), micro-beads (e.g., latex, polystyrene, or other polymer), porous polymer matrices (e.g., polyacrylamide gel, polysaccharide, polymethacrylate), and substrates comprising cellulosic fibers (e.g., cellulose sponges, cellulose paper). In one aspect, the porous or high bind carbon plate is a MSD (Meso Scale Discovery®) high bind plate. The substrate may be a biosensor chip, microarray, or lab-on-chip capable of sensing a target molecule. Any kind of biosensor that is capable of sensing specific binding to the biosensor chip is applicable, including commercially available biosensors, such as the biosensors produced by Biacore.

As used herein, an entity (e.g., antibody, anti-drug antibody, drug, protein, enzyme, antibody, antibody fragment, multiple domain biotherapeutics (e.g., antibody drug conjugates), or related species) that is modified by the term "labeled" includes any entity that is conjugated with another molecule or chemical entity a that is empirically detectable (e.g., "detectable label"). Chemical species suitable as labels for labeled-entities include, but are not limited to, enzymes, fluorescent dyes; quantum dots; optical dyes; luminescent dyes; and radionuclides.

As used herein, the term "one or more" includes at least one, more suitably, one, two, three, four, five, ten, twenty, fifty, one-hundred, five-hundred, etc., of the item to which "one or more" refers.

The approach disclosed herein has been shown to eliminate drug interference in ADA assays. In practice, this method principle can be applied to reduce/eliminate the interferences in any type of immunoassay. This method principle can also be used for any ligand binding assays for ADA, PK and biomarkers. The methods described herein can be applied to ligand binding assays to test for neutralizing antibodies (NAbs). The ligand binding assays can include competitive inhibition of drug binding to drug target. In PK and biomarker assays, excess antibody can be added for complex formation and after precipitation and acid dissociation; detection is made using labeled detection antibody. In all cases, it is important to optimize the concentration of PEG in the assay to balance the sensitivity and specificity. The higher concentration of PEG, the lower molecular weight protein it will precipitate. Therefore, to specifically precipitate desired complex containing target analyte (such as antibody-drug complex precipitation), one needs to minimize the amount on unbound non-specific proteins to be precipitated (such as serum IgM and IgG). The MSD high bind plate was utilized in the studies due to its carbon and porous structure. Based on assay design principle, other large capacity coating surfaces would also work.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
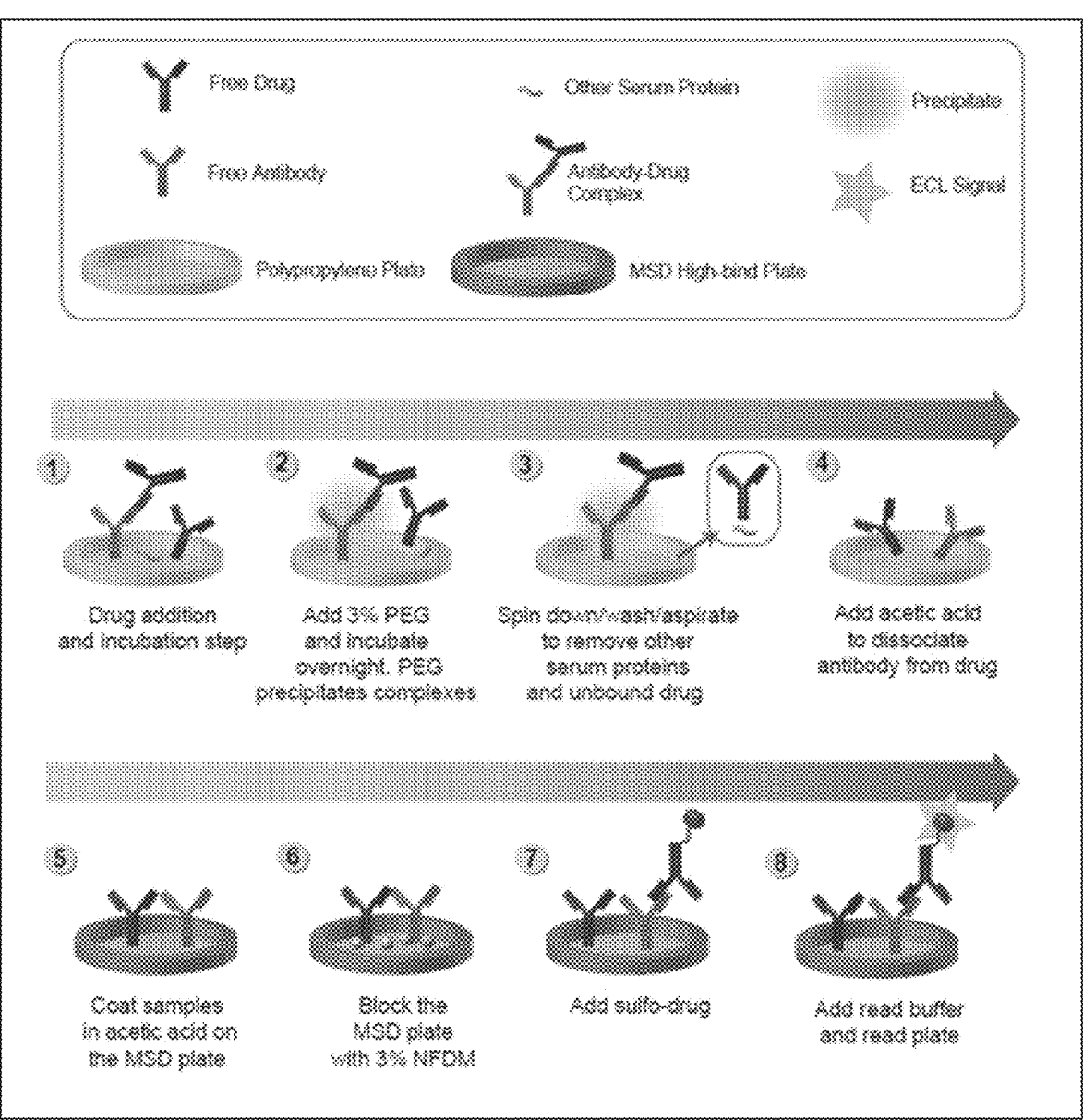
FIG. 1 is a schematic representation of an embodiment of an ADA assay according to the invention.

The present inventors have developed a novel approach for qualitatively and/or quantitatively detecting ADAs from a sample which is effective in reducing and eliminating the interference problems caused by drug or target in ADA detection. Using the principle of PEG precipitation, acid dissociation, coating on high capacity surface under acidic condition, the methods described herein allow for specific detection of ADA as well as drug or drug target using specific detection reagent. The approach can be applied to broader applications for reduction or elimination of inter-ference in immunoassays for ADA, PK/TK, and biomarker (such as drug target) assays, as well as ligand-binding assays for detection of neutralizing antibodies.

For a drug with a long half-life and/or one administered at a high dose or a repeated dose, such as an antibody-based therapy, the ADA usually forms circulating immune com-plexes with the drug, typically making the ADA unavailable for detection. For example, circulating drug may interfere with the detection of ADAs and drug target, or ADAs may interfere with the detection and/or accurate quantitation of drug levels for pharmacokinetic ("PK") studies and or toxicokinetics ("TK") studies. Monoclonal antibody drug interference, especially from human IgG4 drugs, presents an additional challenge for ADA analysis due to its longer half-life and higher doses. The impact of such interference is specific to the immunoassay method and platform and may be dependent on the reagents used in each respective assay. Development of drug tolerant immunogenicity assays becomes more challenging when the drug itself is a human-ized antibody therapeutic.

The most widely adopted approaches in use currently still have limitations of timing, sensitivity or accuracy due to the presence of interference factors that are the same or resemble the binding partners in the ligand assay. These interferences include but not limited to drug interference in the ADA assay, ADA and/or drug target interference in the PK assay, drug interference in the drug target biomarker assay, etc. The commonly used ADA method is the bridging assay where a multi-valent ADA bridges between a capture drug (unlabeled or biotin labeled) and a labeled detection drug. This format is susceptible to endogenous drug interference (false negative ADA) and/or drug target interference (false positive ADA). Being recognized as one of the major challenges in the analytical method development field, many approaches have been used to mitigate this problem such as acid or base dissociation, 3rd party binding partner competitive inhibition, and/or removal of the interference factors, solid phase extraction (SPEAD), ACE and many others. The use of acid dissociation in sample treatment in conjunction with a bridging assay allows for some improvement in the detection of ADAs in the presence of a drug with improved assay sensitivity and ADA recovery. The same is typically observed with the SPEAD and ACE which usually allow for some improvement in drug tolerance; but sensitivity and relative accuracy is not fully maintained. Although acid (or base) dissociate the ADA/drug immune complex, once the mixture is neutralized under the assay condition, the immune complexes re-form. In currently used ADA assays, ADA detection is only possible if the production of ADA exceeds the amount of drug present in the patient's serum due to the formation of ADA-drug complexes. Such drug interference leads to an underestimation of the number of patients of patients producing ADA.

Immunogenicity of drug products, particularly therapeutic proteins, is a major concern in clinical and preclinical studies since it can lead to potentially serious side effects, loss of efficacy, and changes in drug exposure, complicating the interpretation of toxicity, pharmacokinetic (PK) and pharmacodynamics (PD) data. As the number of drug products with long half-life such as monoclonal antibodies is increasing, drug tolerance in ADA assays is of growing concern. To assess the overall immunogenic potential of a drug, the total amount of ADA is of particular interest. Many techniques that are widely used for detection of ADAs in serum and plasma depend on the specific binding of the ADA to its target drug via the antigen binding site. For example, bridging assay formats rely on the availability of the antigen binding sites on ADAs. As these many assay formats rely on the availability of the antigen binding sites on the ADAs, only drug-free or partially drug-free ADA can be detected. Because specific assay materials are sparse and time is pressing, an assay format with improved drug tolerance for detection of ADAs in biological samples is highly desirable Drug tolerance is generally defined as the maximal amount of free drug in a sample that still results in a detectable ADA signal. Acid treatment of samples has been used to improve free drug tolerance in ADA assays. Antibody-antigen (or drug) binding is weakened and eventually disrupted by low pH, making detection of free ADA that is dissociated from partially or completely drug-bound ADAs possible in many immunogenic assay formats (i.e., bridging assay formats), thereby improving drug tolerance. As demonstrated in the examples provided herein, however, acid treatment alone does not eliminate drug tolerance in ADA assays.

In some embodiments, antibody-antigen (or drug) binding is weakened and eventually disrupted by high pH, making detection of free ADA that is dissociated from partially or completely drub-bound ADAs, following treatment with a basic solution, possible in many immunogenic assay formats. The structural characteristics of the biologic drug, such as pI, or the presence of certain conjugating bonds, will dictate whether an acid solution or basic solution is more appropriate for disrupting ADA/drug binding. To increase drug tolerance and provide an improved ADA assay format, the present inventors have developed methods for determining the presence or absence of an ADA in a sample with improved drug tolerance. The methods contemplated herein include a polyethylene glycol precipitation step and an acid dissociation step.

As disclosed herein, the present invention relates to a method for determining the presence or absence of an ADA in a sample (e.g., a biological sample), the method comprising contacting the sample with an excess amount of drug to which the ADA binds to form drug/ADA complexes, contacting the drug/ADA complexes with polyethylene glycol (PEG), to form a precipitate comprising drug/ADA complexes, contacting the precipitate with a solution to dissociate the drug/ADA complexes, immobilizing the dissociated ADAs on a substrate, and determining the presence of or amount of said ADA. In a further aspect, the determining step comprises contacting the immobilized ADAs with drug conjugated to a detectable label and determining the presence of or amount of said detectable label, to thereby determine the presence or absence of ADA in the sample.

In one embodiment, the precipitate (drug/ADA complexes) is contacted with an acid solution to dissociate the complexes and then coated on a large surface (under acidic conditions to keep drug and ADA apart) or substrate (e.g., a high bind carbon plate with high coating capacity) for a time sufficient to allow coating of all dissociated free drugs and free ADAs. The acidic environment prevents the complexes from reforming while being immobilized onto the substrate surface. When an acid solution is used to dissociate the complexes, the assay can be referred to as a PandA (PEG and Acid) assay.

In another embodiment, the final precipitate (drug/ADA complexes) is reconstituted with a basic solution to dissociate the complexes and then coated on a large surface (under basic conditions to keep drug and ADA apart) or substrate (e.g., a high bind carbon plate with high coating capacity) for a time sufficient to allow coating of all dissociated free drugs and free ADAs. The basic environment prevents the complexes from reforming while being immobilized onto the substrate surface.

The selection of an acidic or basic solution will depend on the parameters of the drug (e.g., the biologic drug), such as pI, or the presence of certain conjugating bonds, and the selection will have minimal effect on the integrity and structure of the drug.

The present invention also relates to methods for reducing interference in a drug PK/TK assay due to the presence of an ADA in a biological sample, the method comprising contacting the sample with an excess amount of an ADA to form drug/ADA complexes, contacting the drug/ADA complexes with polyethylene glycol (PEG), to thereby form a precipitate comprising drug/ADA complexes, contacting the precipitate with an acid solution, thereby dissociating the drug/ADA complexes, immobilizing the dissociated free drug and free ADA on a surface and/or substrate, and performing the drug PK/TK assay using specific detection reagent against drug, to thereby reduce interference from the ADA. The drug assay can be, for example, a drug quantitation assay, a drug PK/TK assay or a drug potency assay. Similar principle can be applied to method for quantitation of drug target as biomarker assay for drug safety and efficacy (PD) in the presence of drug interference. Excess drug is added to the sample to form drug target/drug complex. PEG precipitation and acid dissociation (or base dissociation) steps are used and specific drug target detection reagent is then used.

In some aspects the disclosure provides methods for determining the presence or absence of an ADA directed against a drug. The term "drug" or "drug material", as used herein refers to a chemical that has medicinal, performance-enhancing, and/or intoxicating effects when introduced into the body of a human or other animal. For example, the drug can be an organic or inorganic small molecule compound or a biologic therapeutic (e.g., an antibody (e.g., a drug antibody) or fragment thereof, multiple domain biotherapeutics, nucleic acid, peptide, polypeptide, peptidomimetic, carbohydrate, or lipid), so long as the drug is immunogenic and capable of eliciting an immune response. The term "drug antibody" denotes an antibody which can be administered to an individual for the treatment of a disease and as used herein distinguishes such antibodies from ADAs. Non-limiting examples of drug antibodies include, for example, an antibody selected from muromomab-CD3, abciximab, rituximab, daclizumab, basiliximab, palivizumab, infliximab, trastuzumab, etanercept, gemtuzumab, fresolimumab, alemtuzumab, ibritomomab, adalimumab, alefacept, omalizumab, tofacitinib, tositumomab, efalizumab, cetuximab, bevacizumab, natalizumab, ranibizumab, panitumumab, eculizumab mepolizumab, necitumumab, blinatumomab, nivolumab, dinutuximab, secukinumab, evolocumab, pembrolizumab, ramucirumab, vedoluzumab, siltuximab, opinutuzumab, adotrastuzumab emtansine, raxibacumab, pertuzumab, brentuximab, belimumab, ipilimumab, denosumab, tocilizumab, ofatumumab, canakinumab, golimumab, ustekinumab, catumaxomab, and certolizumab.

The methods disclosed herein may comprise a polyethylene glycol ("PEG") mediated precipitation step comprising contacting a sample with a PEG compound. The PEG compound may be a PEG compound having a molecular weight between 1,000 and 40,000 daltons. For example, the PEG compound comprises at least one PEG selected from the group consisting of selected from the group consisting of PEG1000, PEG1450, PEG3000, PEG6000, PEG8000, PEG10000, PEG14000, PEG15000, PEG20000, PEG250000, PEG30000, PEG35000, and PEG40000.

The specific concentration of PEG is selected to maximize the balance of specificity and selectivity. The amount of PEG contacted with the sample may correspond to a concentration of between about 0.1% and about 10.0%, about 0.2% and about 7.0%, between about 0.5% and about 6.0%, between about 0.5% and about 5.0%, between about 1.5% and about 5.5%, between about 2.0% and about 5.0%, between about 3.0% and about 4.5%, between about 3.5% and about 4.0%, between about 1.0% and about 2.5%, between about 1.2% and about 1.5%, or about 0.1%, 0.2%, 0.5%, 1.0%, 1.2%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5% or about 10.0% PEG.

The methods may comprise an acid dissociation step comprising contacting a precipitate with an acid. The acid may be or include an organic acid. Alternatively or in addition, the acid may be or include an inorganic acid. The acid used in the dissociation step may comprise a mixture of an organic acid and an inorganic acid. Non-limiting examples of organic acids include, for example, citric acid, isocitric acid, glutamic acid, acetic acid, lactic acid, formic acid, oxalic acid, uric acid, trifluoroacetic acid, benzene sulfonic acid, aminomethanesulfonic acid, camphor-10-sulfonic acid, chloroacetic acid, bromoacetic acid, iodoacetic acid, propanoic acid, butanoic acid, glyceric acid, succinic acid, malic acid, aspartic acid, and combinations thereof. Non-limiting examples of inorganic acids include, for example, hydrochloric acid, nitric acid, phosphoric acid, sulfuric acid, boric acid, hydrofluoric acid, hydrobromic acid, and mixtures thereof.

The amount of an acid may correspond to a concentration of between about 0.01M to about 10M, between about 0.1M to about 5M, about 0.1M to about 2M, between about 0.2M to about 1M, or between about 0.25M to about 0.75M of an acid or a mixture of acids. In some instances the amount of an acid corresponds to a concentration of greater than or equal to about 0.01M, 0.05M, 0.1M, 0.2M, 0.3M, 0.4M, 0.5M, 0.6M, 0.7M, 0.8M, 0.9M, 1M, 2M, 3M, 4M, 5M, 6M, 7M, 8M, 9M, or 10M of an acid or a mixture of acids. The pH of the acid can be, for example, about 0.1, 0.5, 1.0, 1.5, 2.0, 2.5, 3.0, 3.5, 4.0, 4.5, 5.0, 5.5, 6.0, or 6.5.

The methods may comprise an base dissociation step comprising contacting a precipitate with an base. The base may be or include an organic base. Alternatively or in addition, the acid may be or include an inorganic base. The base used in the dissociation step may comprise a mixture of an organic base and an inorganic base. Non-limiting examples of bases include, for example, urea, sodium hydroxide, rubidium hydroxide, cesium hydroxide, calcium hydroxide, strontium hydroxide, barium hydroxide, zinc hydroxide, lithium hydroxide, acetone, methylamine, and ammonia, and mixtures thereof.

Where a basic solution is used to disrupt the ADA/drug interaction, the amount of base may correspond to a concentration of between about 0.01M to about 5M, between about 0.1M to about 5M, about 0.1M to about 1M, between about 0.2M to about 1M, or between about 0.25M to about 0.75M of a base or a mixture of bases. In some instances the amount of a base corresponds to a concentration of greater than or equal to about 0.01M, 0.05M, 0.1M, 0.2M, 0.3M, 0.4M, 0.5M, 0.6M, 0.7M, 0.8M, 0.9M, 1M, 2M, 3M, 4M, 5M, 6M, 7M, 8M, 9M, or 10M of a base or a mixture of bases. The pH of the base can be, for example, about 8.0, 8.5, 9.0, 9.5, 10.0, 10.5, 11.0, 11.5, 12.0, 12.5 and 13.0.

In some embodiments, the sample is contacted with an acid or base for an amount of time sufficient to dissociate preformed drug/ADA complexes. In certain instances, the sample is contacted (e.g., incubated) with an acid or base for a period of time ranging from about 0.1 hours to about 24 hours, e.g., about 0.2 hours to about 16 hours, about 0.5 hours to about 10 hours, about 0.5 hours to about 5 hours, or about 0.5 hours to about 2 hours. In other instances, the sample is contacted (e.g., incubated) with an acid or base for a period of time that is greater than or equal to about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, or 10 hours. The sample can be contacted with an acid or a base at any temperature that is generally compatible with the method, e.g., 4° C., room temperature (RT), or 37° C. RT can be, for example 22° C. to 26° C., e.g., 23° C., 24° C. or 25° C.

The methods may comprise immobilizing a dissociated ADA and/or drug on a surface and/or substrate. The substrate may comprise a carbon surface, glass surface, silica surface, metal surface, a surface coated with a polymeric material, a surface containing a metallic or chemical coating, a membrane, micro-beads, or a porous polymer matrix. The substrate may comprise a porous carbon surface. In an exemplary embodiment, the substrate is a high bind carbon plate having a large surface and high coating capacity.

The methods may further comprise determining the presence of or amount of an ADA, or the presence of or amount of a drug in the sample. Thus, the disclosure provides antibodies, anti-drug antibodies or drug labeled with a detectable label. Non-limiting examples of detectable labels for any of the methods of the invention include a hapten, an enzyme, an enzyme substrate, an enzyme inhibitors, a fluorophore, a chromophores, luminescent markers, radioisotopes (including radionucleotides) and a member of a binding pair. The intensity of the detectable label can be measured using instruments and devices known to those skilled in the art, including, for example a portable or benchtop fluorometer (e.g., a handheld fluorometer) or a portable or benchtop colorimeter (e.g., a handheld colorimeter).

In some embodiments, the detectable label is an electrochemiluminescent label, including, for example, a SULFO-TAG® label.

The detectable label can be a specific member (a first member or a second member) of a binding pair. Binding pairs for use in the methods provided herein include, for example, biotin/streptavidin, biotin/avidin, biotin/neutravidin, biotin/captavidin, epitope/antibody, protein A/immunoglobulin, protein G/immunoglobulin, protein L/immunoglobulin, GST/glutathione, His-tag/Nickel, antigen/antibody, FLAG/M1 antibody, maltose binding protein/maltose, calmodulin binding protein/calmodulin, enzyme-enzyme substrate, and receptor-ligand binding pairs. In some embodiments, the GlcNac binding protein is conjugated to a first member of binding pair (e.g., biotin, avidin, neutravidn, captavid, antibody, antigen, protein A, protein G, protein L, GST, His-Tag, FLAG, MBP, calmodulin binding protein, an enzyme, a receptor or ligand).

As used herein, the terms "fluorescence label" and "fluorophore" used interchangeably and refer to any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals.

Representative fluorophores for use in the methods provided herein include, for example, green fluorescent protein, blue fluorescent protein, red fluorescent protein, fluorescein, fluorescein 5-isothiocyanate (FITC), cyanine dyes (Cy3, Cy3.5, Cy5, Cy5.5, Cy7), Bodipy dyes (Invitrogen) and/or Alexa Fluor dyes (Invitrogen), dansyl, Dansyl Chloride (DNS-C1), 5-(iodoacetamida) fluorescein (5-IAF, 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, rhodamine dyes (5-carboxyrhodamine 6G hydrochloride, Lissamine rhodamine B sulfonyl chloride, rhodamine-B-isothiocyanate (RITC (rhodamine-B-isothiocyanate), rhodamine 800); tetramethylrhodamine 5-(and 6-) isothiocyanate (TRITC)), Texas Red™, sulfonyl chloride, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, Naphtyl Styryl, 3,3'dipropylthiadicarbocyanine (diS-C3-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, IR-125, Thiazole Orange, Azure B, Nile Blue, Al Phthalocyanine, Oxaxine 1, 4', 6-diamidino-2-phenylindole. (DAPI), Hoechst 33342, TOTO, Acridine Orange, Ethidium Homodimer, N (ethoxycarbonylmethyl)-6-methoxyquinolinium (MQAE), Fura-2, Calcium Green, Carboxy SNARF-6, BAPTA, coumarin, phytofiuors, Coronene, and metal-ligand complexes.

Haptens for use in the methods provided herein include, for example, digoxigenin, and biotin.

Enzymes for use in the methods provided herein include, for example, alkaline phosphatase (AP), beta-galactosidase, horse radish peroxidase (HRP), soy bean peroxidase (SBP), urease, beta-lactamase and glucose oxidase.

In certain aspects, this disclosure provides kits that are adapted for determining the presence or absence of an ADA in a biological sample. The kits may comprise instructions and, in a container, reagents for contacting drug/ADA complexes with polyethylene glycol (PEG), to form a precipitate comprising drug/ADA complexes and reagents for contacting the precipitate with an acid solution to dissociating the drug/ADA complexes; and a substrate suitable for immobilizing the dissociated ADAs or drug on for further analysis.

EXAMPLES

The invention is further described in the following examples, which do not limit the scope of the invention described in the claims.

The examples below describe novel ADA assay methods where complete recovery of an antibody was obtained at the limit of quantitation despite the presence of high levels of the antibody therapeutic. Specifically, three case studies are provided to demonstrate elimination of drug interference in ADA assays for the monoclonal antibody therapeutics (drugs A, B and C).

1.1 Assay Format

To improve the drug tolerance (or eliminate drug interference) of conventional immunogenicity assays, the inventors sought to develop a new method for determining the presence or amount of an ADA in a sample (e.g., a biological sample). The inventors have successfully developed a new method where complete recovery of anti-drug antibody was obtained at the limit of quantitation despite the presence of high levels of drug (the antibody therapeutic). A schematic representation of an exemplary embodiment of the method is shown in FIG. 1.

As depicted in FIG. 1, excess drug material is added to a sample (e.g., a biological sample) to allow drug/ADA complexes to form. Following the initial incubation, PEG is added to each sample and incubated to allow for precipitation of complexes. After a series (e.g., one or more) of washes, the precipitate is reconstituted with an acid solution to dissociate drug/ADA complexes. The dissociated drug/ADA complexes are coated on a substrate (i.e., coated on the ells of a high bind MSD plate). Following incubation, the substrate is blocked and then detection is performed using drug labeled with a detectable label allowing for ADA detection by ECL ("electrochemiluminescence) or "enhanced chemiluminescence").

In one aspect, the method depicted in FIG. 1 comprises adding excess drug material to the samples to saturate free antibody therefore forming drug/ADA complexes. The complexes are then precipitated using PEG. PEG is added to the sample at a concentration optimized to achieve the desired sensitivity while maintaining specificity. After a series of washes, the final precipitate is reconstituted with an acid solution and coated on a high bind carbon plate. The acidic environment prevents the complexes from reforming while being absorbed onto the porous carbon surface of the MSD high bind plate. Detection of the total ADA levels is then performed using SULFO-TAG® label conjugated drug followed by Electrochemiluminescence read out on a MESO SCALE DISCOVERY® Sector 2400 reader.

1.2 Experimental Materials

Therapeutic monoclonal antibodies SULFO-TAG® drug, and affinity purified rabbit anti-drug are developed by Genzyme, a Sanofi Company (Framingham, MA). Naive human serum pools from healthy individuals were purchased from Bioreclamation Inc. Disease baseline serum samples were obtained from treatment naïve subjects enrolled in product-related clinical trials. High Bind 96-well Meso Scale plates, Sulfo Tag, read Buffer T, Sector 2400 reader attained from MESO SCALE DISCOVERY® ("MSD"). PEG8000 was obtained from TekNova. Glacial acetic acid was provided by J. T Baker. TWEEN® 20 and Non-Fat Dry Milk-Sigma, acquired from Aldrich. The ELx405 plate washer was supplied by Biotek. Plate wash buffer came from PerkinElmer. Clear polypropylene 96-well microtiter plates were procured from Corning. Bovine Serum Albumin was obtained from Seracare. Borate is found through Sigma Aldrich, Catalog number B0394.

Drug A is a humanized IgG1 depleting antibody that binds to lymphocyte cell surface target for an autoimmune disease. Drug B is a full human IgG4 that neutralizes a soluble cytokine binding to its cell surface receptor in the target tissue for a fibrosis indication. Drug C is a humanized IgG4 that recognizes cell surface adhesion molecule and blocks its binding to a soluble ligand.

1.3 Bridging Immunoassay Without Acid Dissociation Procedure

The MSD bridging assay format requires the drug to be labeled with biotin and labeled with SULFO-TAG®. According to the MSD assay format, the biotinylated drug will serve as the capture molecule and the SULFO-TAG® labeled drug will be the reporter in the bridging assay.

Samples are initially diluted 1:10 in assay buffer ((300 mM Acetic acid, 2% BSA). Samples are added to a polypropylene plate in duplicate wells and a solution containing equi-molar concentrations of Biotin-Drug and SULFO-TAG® Drug in assay buffer is added. The plate is then incubated for 2 hours in a 22-26° C. shaker at 450 rpm. A streptavidin coated MSD plate is blocked with assay buffer for a minimum of one hour. Following the incubation, the MSD plate is washed 3 times and 50 µL of the incubated mixture is transferred from the polypropylene plate to the MSD plate and incubated for 2 hours on a 22-26° C. shaker. Following the incubation, the plate is washed and a solution of MSD read buffer T containing tripropylamine is added and the plate is read on the MSD sector imager 2400.

Within the instrument, a voltage is applied. In the presence of tripropylamine, SULFO-TAG® participates in an electro-chemiluminescent (ECL) reaction. The antibodies bridging the SULFO-TAG®-Drug and the Biotin-Drug bound to the streptavidin surface will result in an ECL signal. After the final incubation, the plate is washed with 0.05% TWEEN® in PBS. Read buffer T 2× is then added and the plate is read on a Sector PR2400. The electro-chemiluminescent signal is proportional to the anti-drug antibody in each sample. Sample results are converted to a signal to background ratio (S/B) by dividing the average ECL signal from an individual sample by the average ECL signal of the negative control.

1.4 Bridging Immunoassay With Acid Dissociation Procedure

Samples are initially diluted 1:10 in assay buffer (300 mM Acetic acid, 2% BSA) in incubated at 22-26° C. for 45 minutes. Samples are then added to a polypropylene plate in duplicate wells and a solution containing equi-molar concentrations of Biotin-Drug and SULFO-TAG®-Drug in assay buffer in addition to Tris HCL is added at a ratio to effectively neutralize the pH to 7.0. The plate is then incubated for 2 hours in a 22-26° C. shaker at 450 rpm. A streptavidin coated MSD plate is blocked with assay buffer for a minimum of one hour. Following the incubation, the MSD plate is washed 3 times and 50 µL of the incubated mixture is transferred from the polypropylene plate to the MSD plate and incubated for 2 hours on a 22-26° C. shaker. Following the incubation, the plate is washed and a solution of MSD read buffer T containing tripropylamine is added and the plate is read on the MSD sector imager 2400.

Within the instrument, a voltage is applied. In the presence of tripropylamine, SULFO-TAG® participates in an electro-chemiluminescent (ECL) reaction. The antibodies bridging the SULFO-TAG-Drug and the Biotin-Drug bound to the streptavidin surface will result in an ECL signal. After the final incubation, the plate is washed with 0.05% TWEEN® in PBS. Read buffer T 2× is then added and the plate is read on a Sector PR2400. The electro-chemiluminescent signal is proportional to the anti-drug antibody in each sample. Sample results are converted to a signal to background ratio (S/B) by dividing the average ECL signal from an individual sample by the average ECL signal of the negative control.

1.5 PEG and Acid (PandA) Procedure 1

Samples are initially diluted 1/5 in assay buffer (300 mM Acetic acid, 2% BSA) containing excess drug (10-50 ug/mL) and incubated for one hour at 37° C. with 450 rpm in a polypropylene plate to allow complexes between drug and any remaining free antibody in the sample. This is followed by the addition of 3% PEG in Borate pH 8.0 to each sample and an overnight incubation at 2-8° C. The final concentration of PEG buffer in each sample is 1.5%.

The following day, the plate is centrifuged at 4000 rpms for 20 minutes to precipitate the complexes into a pellet. The pellets are then re-suspended with 1.5% PEG in Borate pH 8.0 and centrifuged a second time at 4000 rpms for 20 minutes. The wash cycle is repeated three times. Following the final centrifugation, each sample suspended in 100 µl of 300 mM acetic acid and further diluted 1/10 (20 µl sample+ 180 µl acetic acid) for a final sample dilution of 1/50. Diluted samples are then coated by adding 25 µl in duplicate to wells of an MSD high bind plate and incubated for one hour at 24° C. shaking at 450 rpm. Following the incubation, the plate is washed with 1× plate wash buffer and blocked with 3% milk in PBS for one hour at 24° C. shaking; after which, the plate is washed and 100 ng/ml of SULFO-TAG®-Drug was added to the samples and incubated for one hour at 24° C. shaking. After the final incubation, the plate is washed with 0.05% TWEEN® in PBS. Read buffer T 2× is then added and the plate is read on a Sector PR2400. The electrochemiluminescent signal is proportional to the anti-drug antibody in each sample.

In some embodiments, the incubation step following the initial acid addition can be carried out at 23° C., 25° C., 27° C., 30° C., 32° C., 35° C., 37° C., 39° C. or higher.

In some embodiments, following the final precipitation step, each sample can be further diluted to a final sample dilution of, e.g., 1:5, 1:10, 1:20, 1:25, 1:30, 1:40, 1:50, or 1:60, 1:80, 1:100, or 1:200. Typically the final sample dilution will be <1:100, which is the minimal required dilution (MRD) set by the Food and Drug Administration (FDA).

1.5 PEG and Acid (PandA) Procedure 2

Samples are initially diluted 1/5 in assay buffer (300 mM Acetic acid, 2% BSA) containing excess drug (10-50 μg/mL) and incubated for one hour at 24° C. with 450 rpm in a polypropylene plate to allow complexes to form between drug and any remaining free antibody in the sample. This is followed by the addition of a PEG solution at a 1:1 PEG: sample ratio to each sample and an overnight incubation at 2-8° C. The final concentration of PEG was optimized for each product to be optimal for precipitation of specific complexes and achieving the desired specificity and sensitivity while minimizing the effect of un-complexed molecules such as non-specific IgGs. The PEG concentrations added to the samples were between 3% and 6% (3% for drug A and 6% for drug B and C added at a 1:1 ratio to diluted samples).

The following day, the plate is centrifuged at 4000 rpms for 30 minutes to precipitate the complexes into a pellet. The pellets are then re-suspended with PEG in PBS and centrifuged a second time at 4000 rpms for 20 minutes. The wash cycle is repeated one additional time. Following the final centrifugation, each sample is re-suspended and diluted in 300 mM acetic acid to achieve the final MRD desired for the particular assay (1/50 for Drug A and C and 1/25 for drug B). Samples are then coated in duplicate wells of an MSD high bind plate. The plate is then incubated for one hour at 24° C. shaking at 450 rpm. Following the incubation, the plate is washed with 1× plate wash buffer and blocked with 3% milk in PBS for one hour at 24° C. shaking. The plate is then washed and a solution containing SULFO-TAG®-Drug is added to the samples and incubated for one hour at 24° C. shaking. After the final incubation, the plate is washed with 1× plate wash buffer. Read buffer T 2× is then added and the plate is read on a Sector PR2400. The electro-chemiluminescent signal is proportional to the anti-drug antibody in each sample.

In some embodiments, the incubation step following the initial acid addition can be carried out at 23° C., 25° C., 27° C., 30° C., 32° C., 35° C., 37° C., 39° C. or higher.

In some embodiments, following the final precipitation step, each sample can be further diluted to a final sample dilution of, e.g., 1:5, 1:10, 1:20, 1:25, 1:30, 1:40, 1:50, or 1:60, 1:80, 1:100, or 1:200. Typically the final sample dilution will be <1:100, which is the minimal required dilution (MRD) set by the Food and Drug Administration (FDA).

2.1 Drug A

Sensitivity and Drug Tolerance Assessment

For Drug A, the PandA method was compared to the traditional MSD bridging assay with and without acid dissociation to improve drug tolerance. Assay sensitivity and drug Tolerance were determined using affinity purified rabbit anti-drug at concentrations ranging from 8 μg/mL to 125 ng/mL with and without drug (Drug A) at various concentrations (0, 0.1, 10 and 100 g/mL) in the MSD bridging assay format with (FIG. 2A-B) and without acid (FIG. 3A-B) dissociation. The samples containing ADA and drug were prepared in pooled normal human sera and incubated for at least one hour at 37° C. allowing drug/ADA complexes to form prior to assaying.

Cut point was determined by evaluating 40 normal human serum samples, calculating the mean and the standard deviation for the samples and calculating the 95th percentile factor of 1.645-times the standard deviation and adding it to the mean as is typically recommended. For drug A, the new method was compared to the traditional bridging assay with and without acid dissociation for drug tolerance.

Figure 2A:
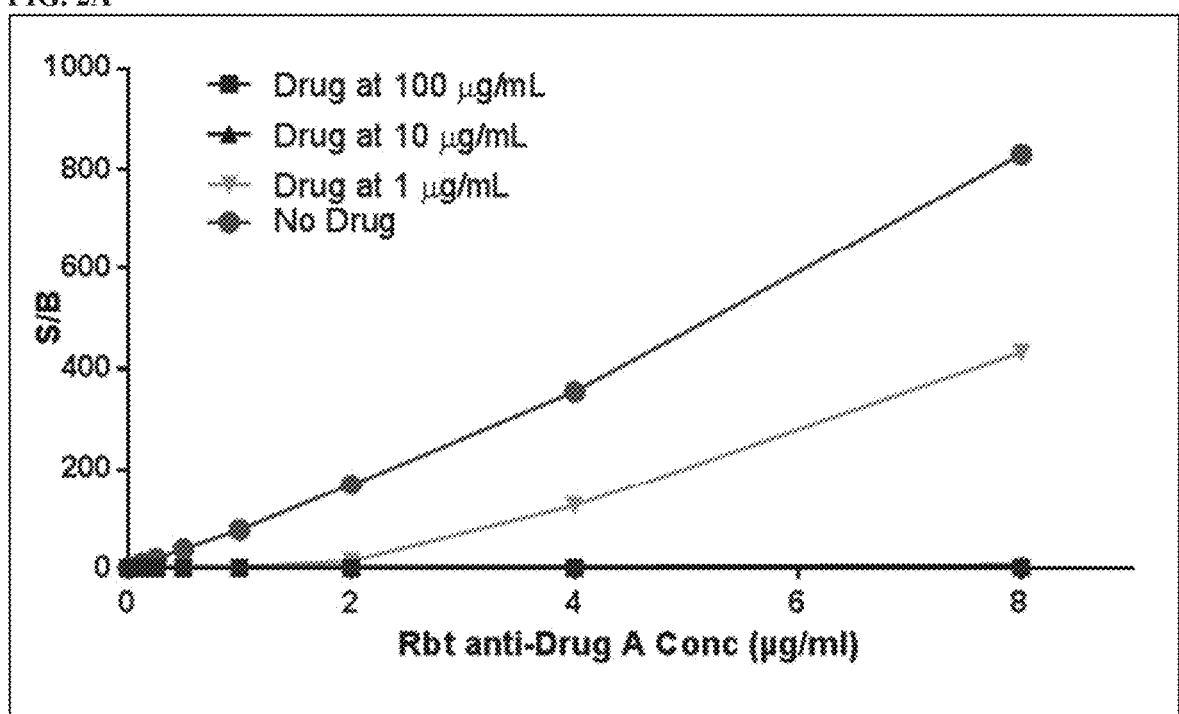
FIGS. 2A and 2B are graphs depicting the results of an example bridging assay format detecting affinity purified rabbit antibody at levels ranging from 8 μg/mL to 125 ng/ml with various concentration of Drug A (0, 1, 10 and 100 μg/mL) tested in the MSD bridging assay format without acid dissociation. A. The observed S/B was plotted against the ADA concentration to assess the recovery of the antibody with different levels of drug compared to baseline without drug. B. Percent recovery relative to baseline. ADA: MSD bridging assay: MESO SCALE DISCOVERY® bridging; S/B: Signal-to-background.
Figure 2B:
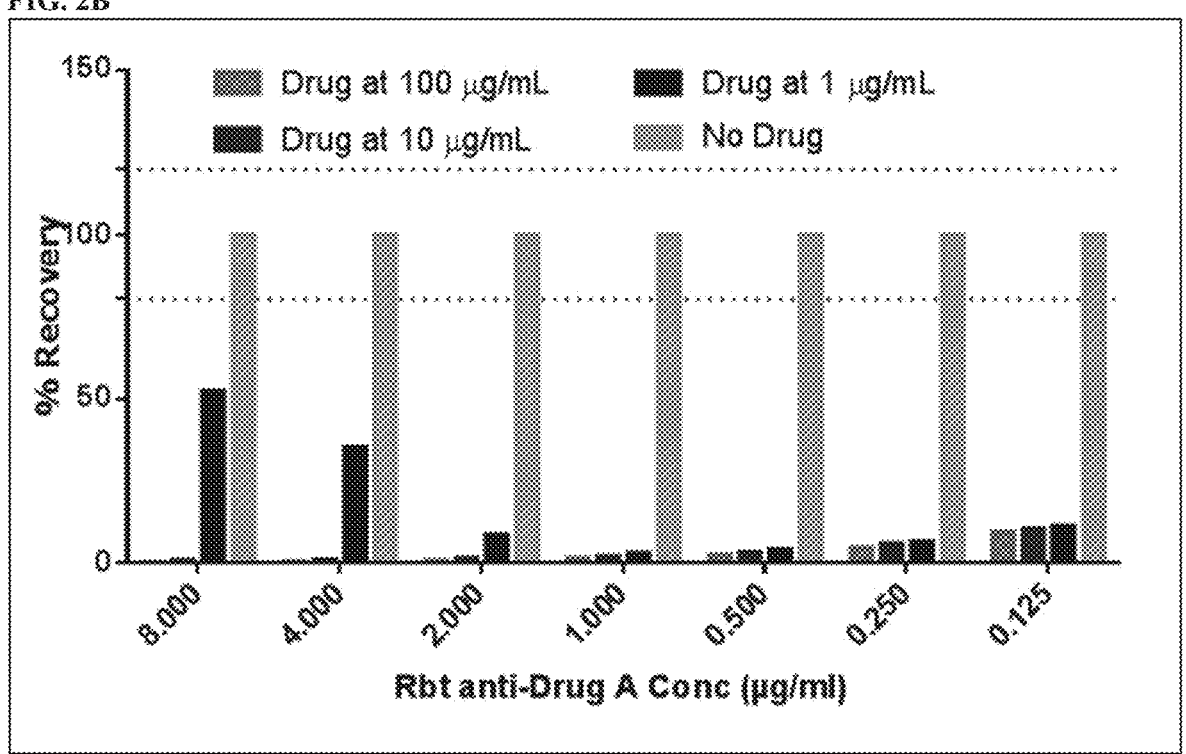

FIG. 2 is a summary of the data comparing the MSD bridging assay format without acid dissociation. The results indicate a strong dose response for ADA detection in the absence of drug and inhibition seen with lug/mL of drug. (FIG. 2A) FIG. 2B indicates low recoveries of antibody detection, approximately 10% at the 125 ng/ml of ADA at the lowest concentration of drug tested of 1 μg/mL. (FIG. 2B) The assay sensitivity was reduced from 15 ng/mL in the absence of drug to 342 ng/ml with 1 μg/mL of drug. The sensitivity in the presence of 100 μg/mL of drug was reduced to 5143 ng/ml or 5.1 μg/mL.

Figure 3A:
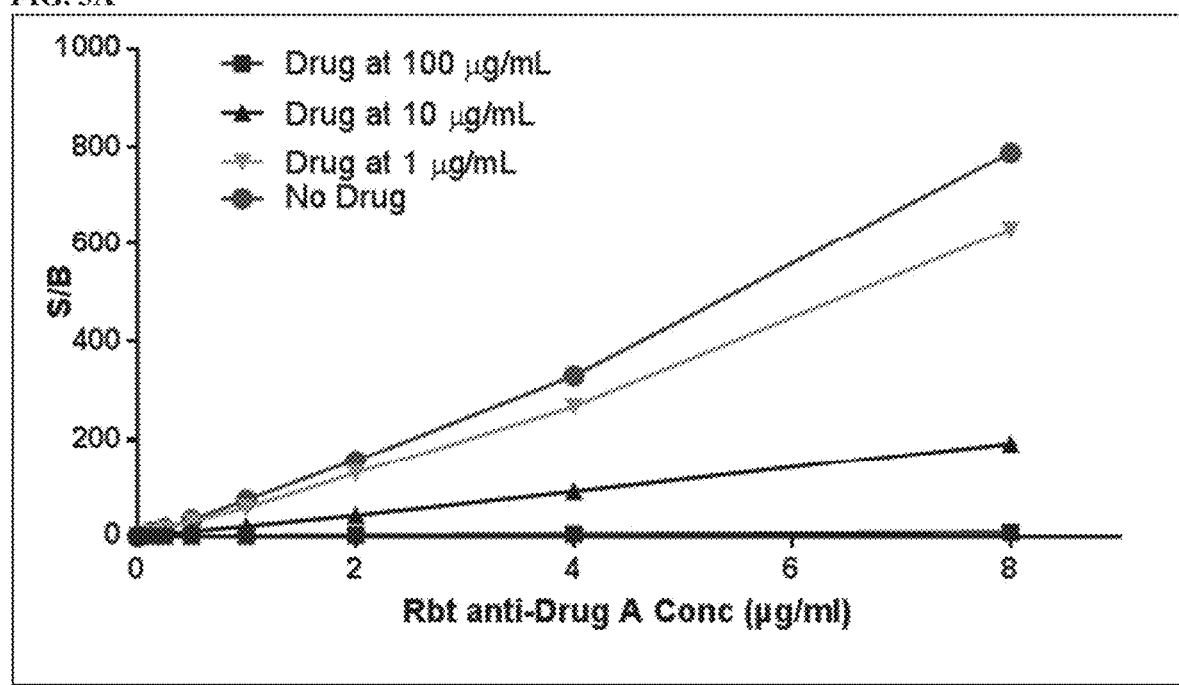
FIGS. 3A and 3B are graphs depicting the results of an example bridging assay format detecting affinity purified rabbit antibody at levels ranging from 8 μg/mL to 125 ng/mL with various concentration of Drug A (0, 1, 10 and 100 μg/mL) tested in the MSD bridging assay format with acid dissociation. A. The observed S/B was plotted against the ADA concentration to assess the recovery of the antibody with different levels of drug compared to baseline without drug. B. Percent recovery relative to baseline. S/B: Signal-to-background.
Figure 3B:
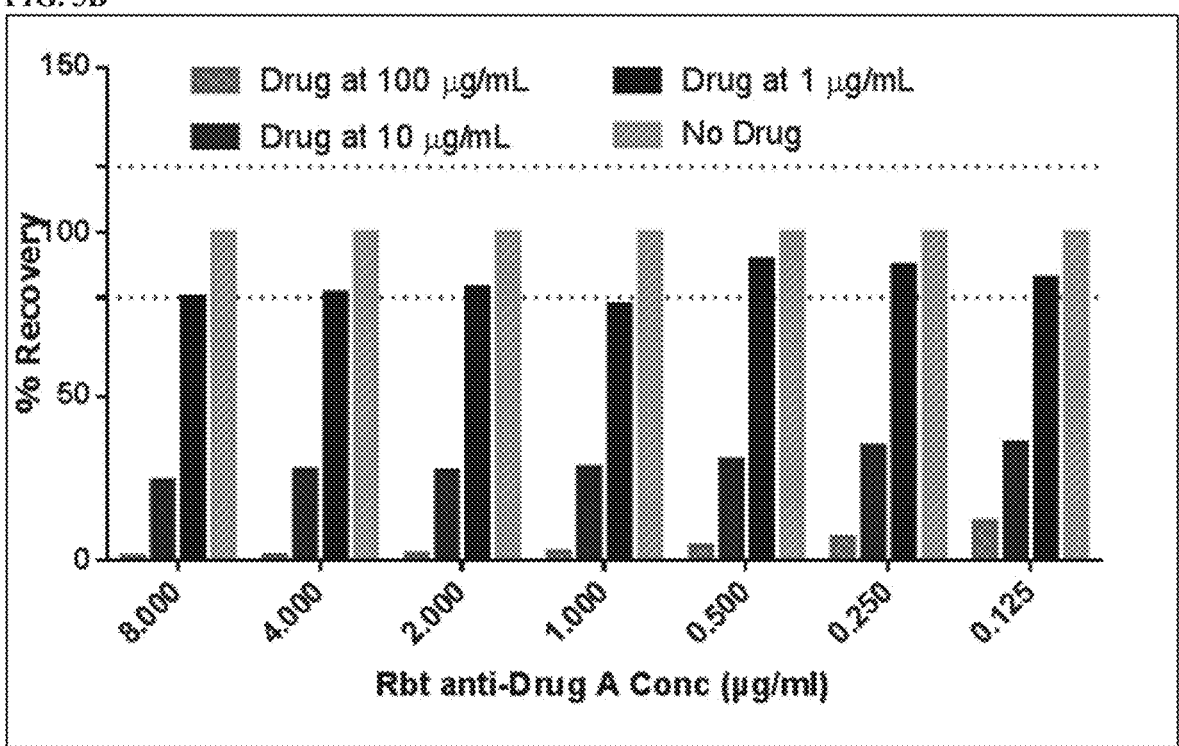

FIG. 3 is a summary of the data from the MSD bridging assay format with acid dissociation. The results indicate a similar dose response to the bridging assay without acid for ADA detection in the absence of drug and inhibition seen with lug/mL of drug. (FIG. 3A) The percent recoveries remained acceptable with lug/mL of drug but reduced to 35% at the 125 ng/ml of ADA at the 10 μg/mL of drug which is lower than the drug Cmax. (FIG. 3B) The assay detection sensitivity was maintained for the 1 and 10 μg/mL of drug at around 15 ng/mL while found to be 262 ng/ml in the presence of 100 μg/mL of drug. Although the sensitivity of the assay meets some proposed guidelines of 250-500 ng/mL in this method, this finding is specific to this product and antibody combination and may not be acceptable for other products or with different antibody controls.

Figure 4A:
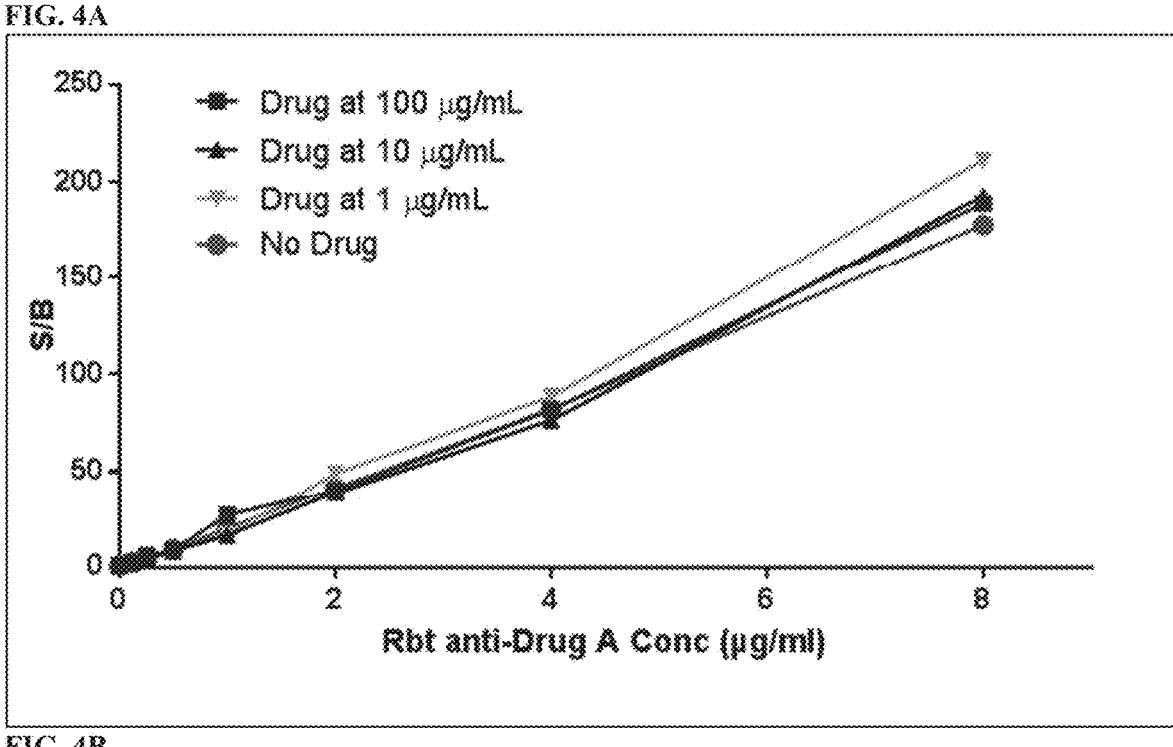
FIGS. 4A and 4B are graphs depicting the results of an example bridging assay format detecting affinity purified rabbit antibody at levels ranging from 8 μg/mL to 125 ng/ml with various concentration of Drug A (0, 1, 10 and 100 μg/mL) tested in the MSD bridging assay using the poly-ethylene glycol precipitation and acid dissociation assay format of the invention (i.e., the PandA assay format). A. The observed S/B was plotted against the ADA concentration to assess the recovery of the antibody with different levels of drug compared to baseline without drug. B. Percent recovery relative to baseline. S/B: Signal-to-background.
Figure 4B:
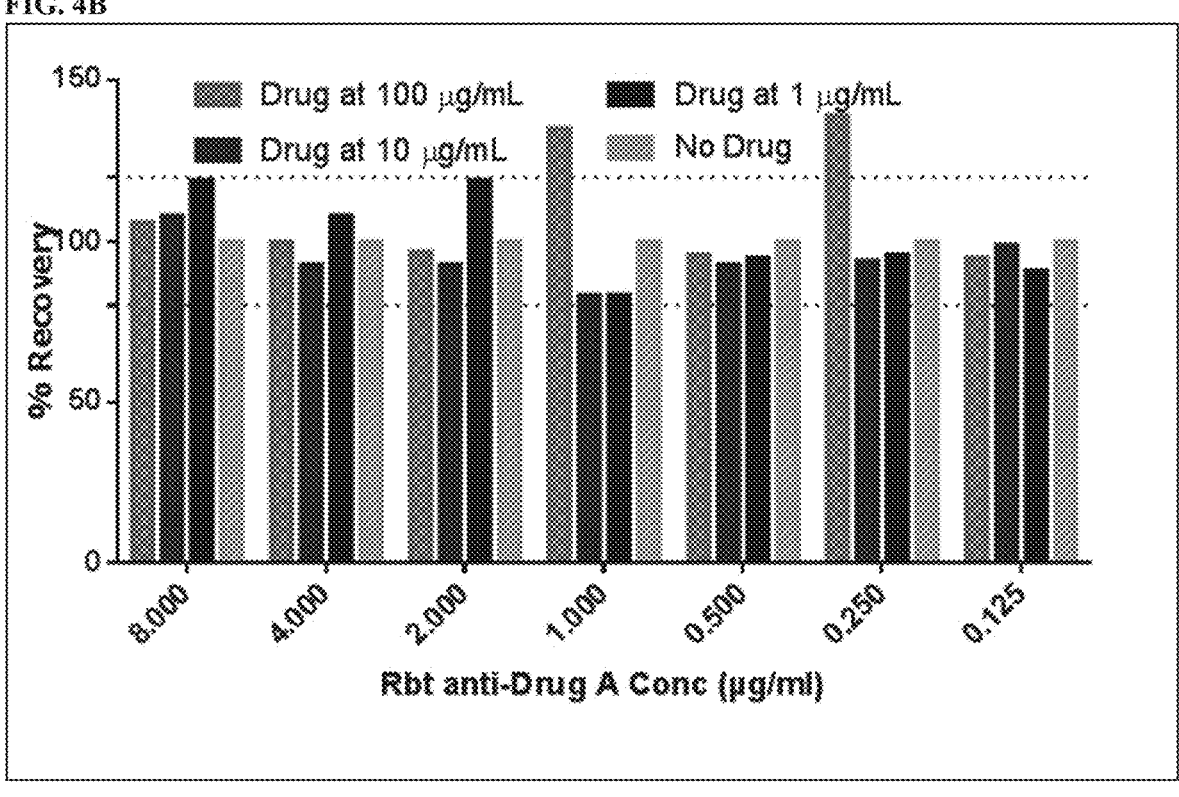

FIGS. 4A and 4B are a summary of the data from the PandA (Procedure 2) precipitation format. The results indicate an acceptable dose response in the absence of drug and no significant inhibition seen due to drug present in the samples. (FIG. 4A) The percent recoveries remained acceptable mostly between 80-120% regardless of the drug amount present in the samples when compared to the sample results with no drug as a reference. (FIG. 4B) Similarly, the assay detection sensitivity was maintained at 9-14 ng/mL despite drug present at 100 μg/mL which is 3-4 folds higher than the expected Cmax of Drug A.

Table 1 is a summary of the assay sensitivities for ADA detection at various concentrations of Drug A tested in each of the methods tested. The assay sensitivity concentrations were obtained by back fitting the S/B cut point from each antibody curve shown in FIGS. 2A, 3A and 4A. ADA: Anti-drug antibody; S/B: Signal-to-background.

TABLE 1

| | Assay Sensitivity ng/mL | | |
| Drug (μg/mL) | Bridging Assay without Acid Dissociation | Bridging Assay with Acid Dissociation | PandA method |
|---|---|---|---|
| 0 | 15 | 15 | 10 |
| 1 | 342 | 8 | 13 |
| 10 | 393 | 16 | 9 |
| 100 | 5143 | 262 | 14 |

As shown in Table 1, the PandA method not only improved the drug tolerance but also maintained the assay sensitivity at 9-14 ng/ml despite presence of 100 μg/mL of Drug. Antibody detection recovery remained mostly between 80 and 120% regardless of the amount of drug present in the sample, which is superior to the bridging immunoassay with acid dissociation.

Titer Results Comparison

The PandA method can also be used to accurately report antibody titers in the presence of drug. To determine whether end point titers correlate between samples that contain antibody alone (0 µg/ml drug) and others that contain an equivalent amount of antibody but high drug concentration (100 µg/mL drug), test samples were analyzed in the method where dilutions for titration were performed following two different titration schemes. The first scheme incorporated a titration prior to PEG precipitation and the second scheme incorporated the titration prior to coating on the high bind plates. The end point titers were identical between the no drug and drug containing samples at the same antibody level as well as between the titration schemes based on the assay titer cut point value (S/B of 1.2). The end point titer data is summarized in Table 2.

TABLE 2

| | Sample | | | |
|---|---|---|---|---|
| | A | | B | |
| | DRUG Level µg/mL | | | |
| | 100 | 0 | 100 | 0 |
| Titer (diluted pre-PEG) | 1600 | 1600 | 400 | 400 |
| Titer (diluted post-PEG) | 1600 | 1600 | 200 | 400 |

3.1. MSD High Bind Plates (Lot to Lot) and Overall Precision

To determine whether MSD High Bind plates contribute to assay variability, coating of samples was performed on three different lots. Data was plotted and analyzed for equivalence using ANOVA.

Figure 5:
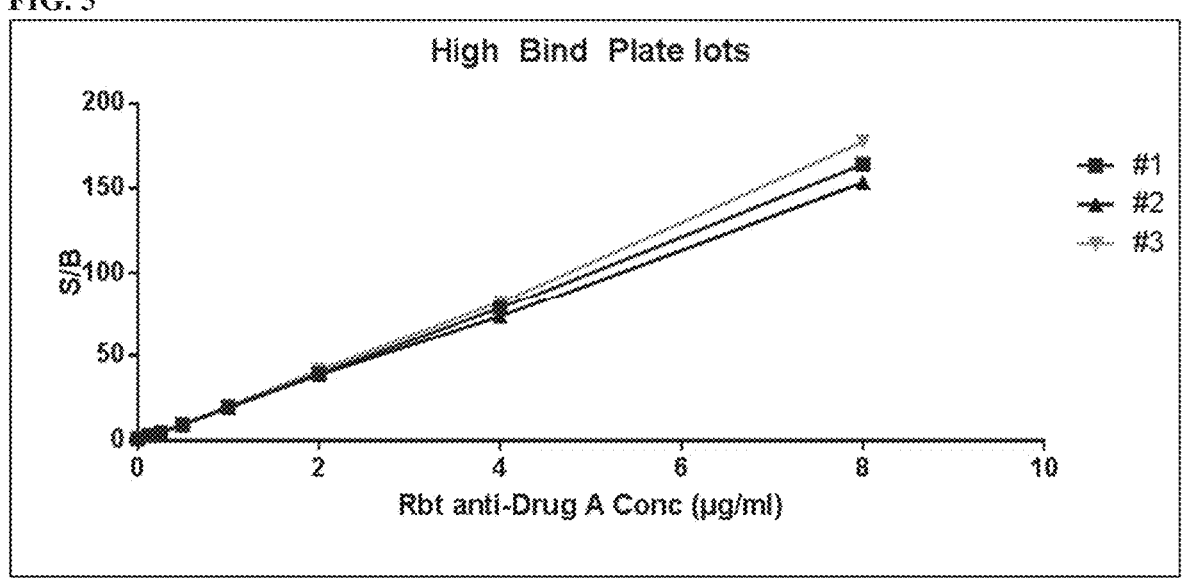
FIG. 5 is a graph depicting the results of an example bridging assay format detecting affinity purified rabbit anti-Drug A antibody with no drug tested in the PEG and Acid (PandA) assay format using three different lots of MSD high bind plates. The observed S/B was plotted against the ADA concentration. ADA: Anti-drug antibody; S/B: Signal-to-background.

To determine whether MSD High Bind plates contribute to the assay variability, coating of samples was performed on three different MSD plate lots. The samples contained affinity purified rabbit antibody with various concentrations of drug. The observed S/B was plotted against the ADA concentration for each of the three lots of plates as shown in FIG. 5. The precision between plate lots was found to be acceptable with CV less than 20% (Table 3) and ANOVA showed no significant differences between the three lots with a p-value of 0.1776.

4.1 Drug B

Target Interference in MSD Bridging Assay with Acid Dissociation

For Drug B, a specific challenge was seen in the MSD bridging assay with acid dissociation since the target for Drug B changes from a monomer to a dimer at low pH causing false positive results. The dimerization effect is seen in 100% of normal serum samples and disease baseline samples in the MSD bridging assay with acid dissociation. This phenomenon was similar to what was reported by Dai et al. [Dai S, Schantz A, Clements-Egan A, Cannon M, Shankar G: Development of a method that eliminates false-positive results due to nerve growth factor interference in the assessment of fulranumab immunogenicity. AAPS J. 16 (3), 464-477 (2014)] where it was found that high apparent incidence of anti-drug antibody (ADA) in phase 1 studies was the result of detection of drug target, a homodimer, due to its ability to bridge drug molecules. Dai et al. found that the acid-dissociation-based pretreatment of samples used for mitigating drug interference dramatically increased drug target interference.

To demonstrate the effect of endogenous target dimerization of the drug target due to acid dissociation and false positive results in the assay, normal (n=32) and baseline disease (n=16) serum samples were analyzed in the bridging assay with and without acid dissociation to highlight the effect of endogenous target dimerization due to acid dissociation and false positive results in the assay.

Figure 6:
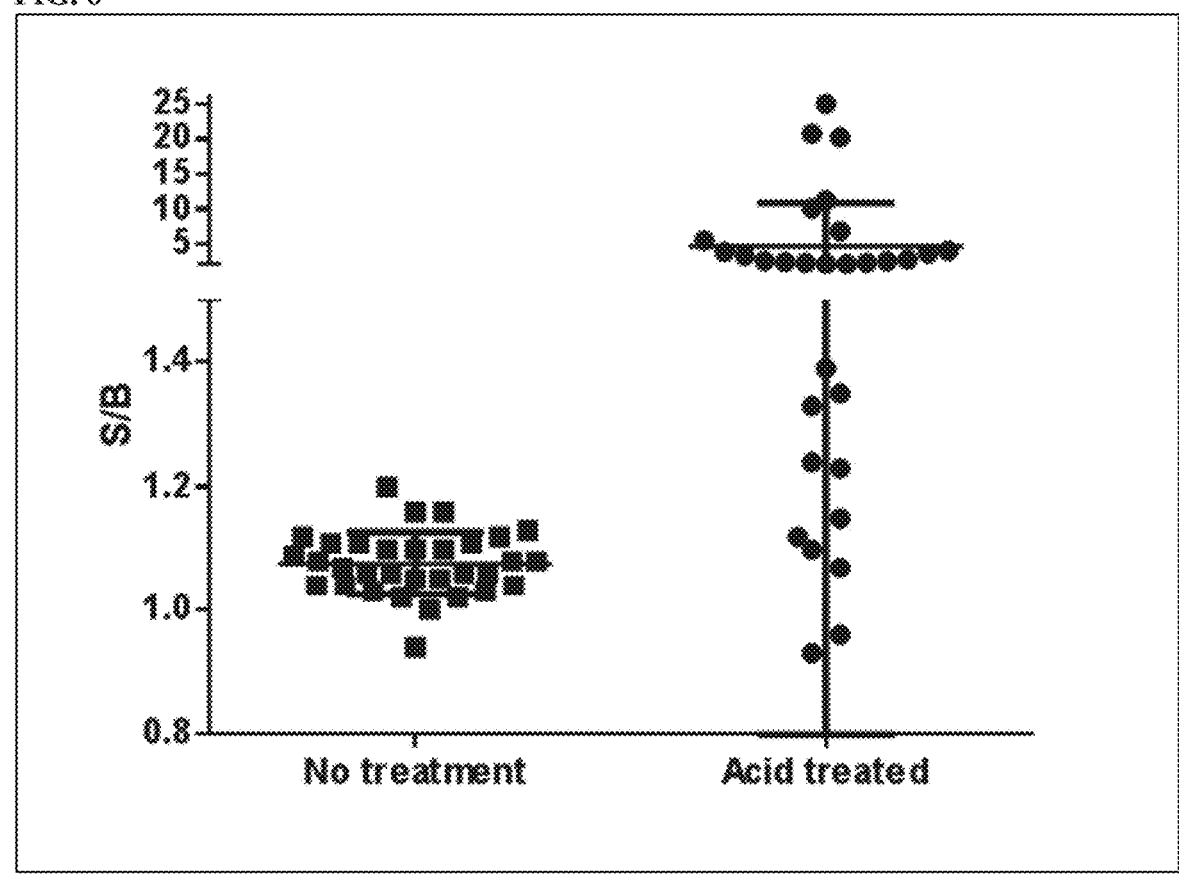
FIG. 6 is a graph depicting the results of an example bridging assay format detecting Drug B ADAs in pooled normal serum samples (n=32) evaluated in the MSDB assay format with and without acid dissociation. Normal Population Distribution (Drug B bridging assays). No treatment=without dissociation; Acid Treated=with acid dissociation; S/B: Signal-to-background.

FIG. 6 is a representation of the normal serum samples tested in the MSD bridging assay with and without acid dissociation. A normal distribution at or near the background of the assay is observed (population on the left) in the non-acid treated set while some positive results were observed with S/B greater than 20 when acid dissociation was applied to the bridging assay.

Figure 7:
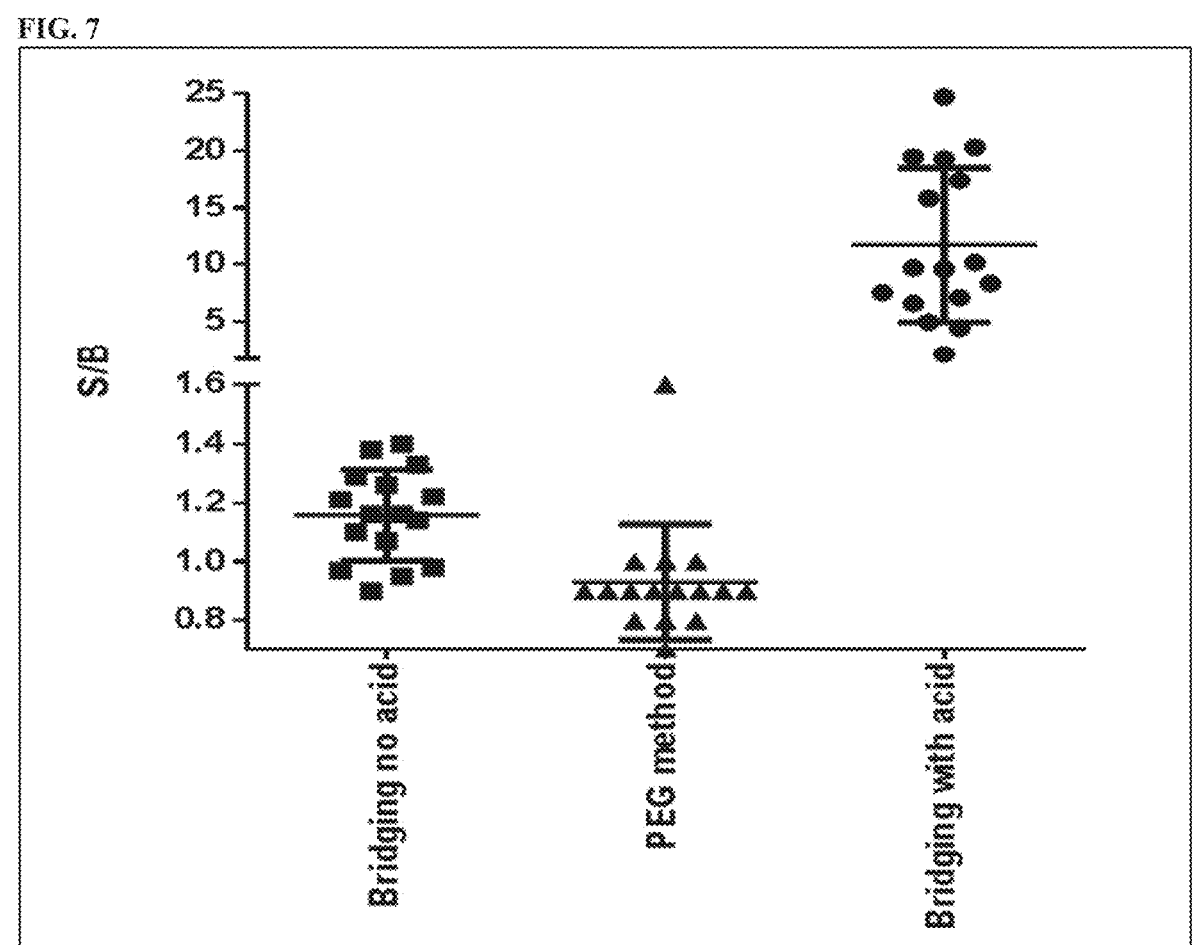
FIG. 7 is a graph depicting the results of an example bridging assay format detecting Drug B ADAs in pooled disease baseline serum samples (n=16) evaluated in the MSD bridging assay format with and without acid dissociation, as well as the PandA assay format to determine population distribution.

FIG. 7 is a representation of disease baseline serum samples when analyzed in the MSD bridging assay without and with acid dissociation as well as the PEG and Acid (PandA) method. Results were comparable between the MSD bridging without acid treatment and PandA method while the acid treatment resulted in higher S/B levels for the majority of the samples tested suggesting interference from drug target due to the dimerization effect at low pH.

As shown in FIGS. 6 and 7, for Drug B, the bridging assay with acid dissociation is not a feasible approach in normal or disease population due to the dimerization of the drug target at lower pH causing false positive results for all samples with results proportional to the amount of endogenous target. For that reason, the assay sensitivity and drug tolerance for Drug B was only compared between the PandA method and the existing MSD bridging assay without acid dissociation.

FIGS. 8A-B and 9A-B are summaries of the data for Drug B comparing the bridging assay format without acid dissociation to the PEG and Acid method (PandA).

Figures 8A, 8B:
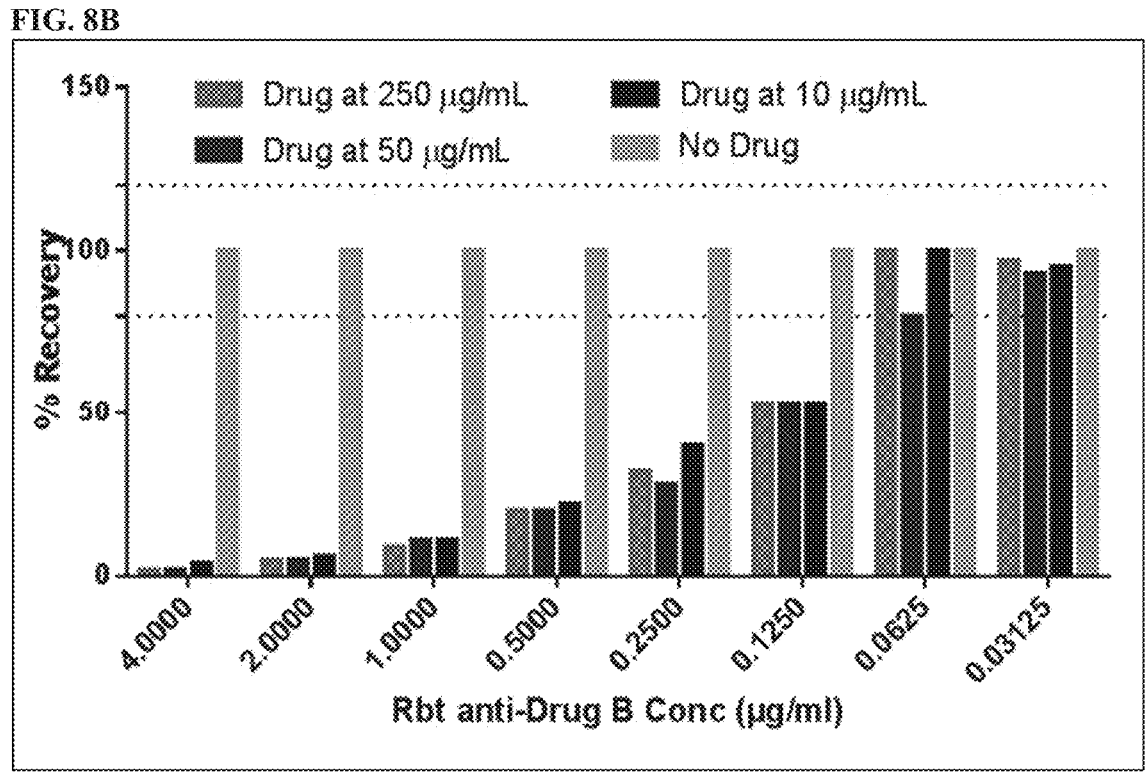
FIGS. 8A and 8B are graphs depicting the results of an example bridging assay format detecting affinity purified rabbit antibody at levels ranging from 4 μg/mL to 31.3 ng/mL with various concentration of Drug B (0, 10, 50 and 250 μg/mL) tested in the MSD bridging assay format without acid dissociation. A. The observed S/B was plotted against the ADA concentration to assess the recovery of the antibody with different levels of drug compared to baseline without drug. B. Percent recovery relative to baseline. S/B: Signal-to-background.

In FIG. 8A, the MSD bridging assay format resulted in an acceptable dose response for ADA detection in the absence of drug and complete inhibition seen with 10 µg/mL and a decrease of sensitivity from 47 ng/ml in the absence of drug to 2 µg/mL of antibody with 10 µg/mL of drug.

For Drug B, the bridging assay without acid dissociation sensitivity was validated at 50 ng/mL with poor drug tolerance. Levels of drug at 250 ng/ml inhibited detection of anti-Drug B antibodies at 250 ng/ml and levels of drug at 1 g/mL inhibited detection of the antibody at 500 ng/mL.

Figure 9A:
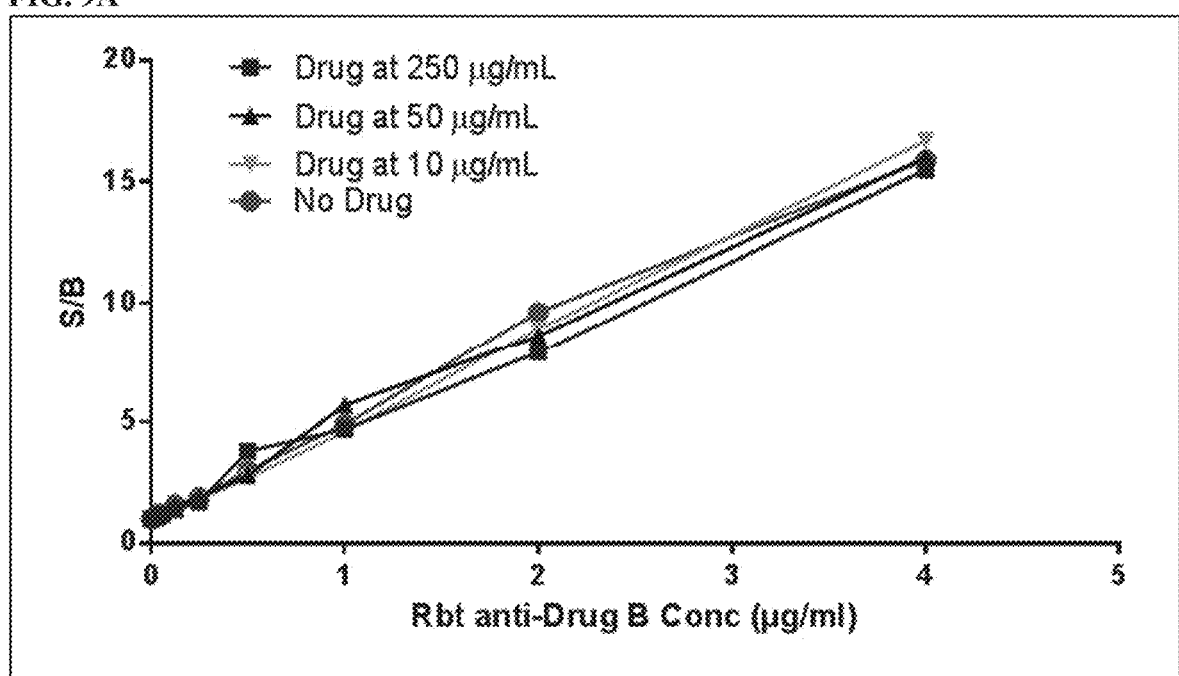
FIGS. 9A and 9B are graphs depicting the results of an example bridging assay format detecting affinity purified rabbit antibody at levels ranging from 4 μg/mL to 31.3 ng/ml with various concentration of drug B (0, 10, 50 and 250 μg/mL) tested in the MSD bridging assay using the PandA assay format. A. The observed S/B was plotted against the ADA concentration to assess the recovery of the antibody with different levels of drug compared to baseline without drug. B. Percent recovery relative to baseline. S/B: Signal-to-background.
Figure 9B:
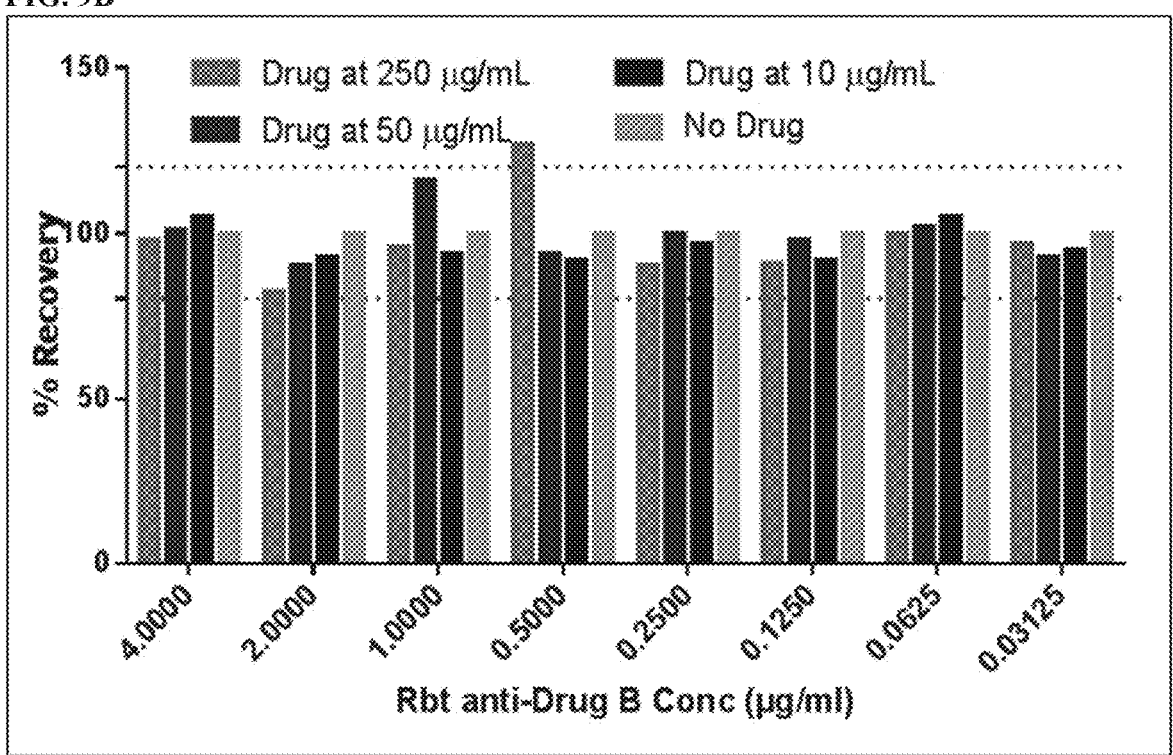

FIGS. 9A-B are a summary of the data from the PandA precipitation format. The results indicate an acceptable dose response in the absence of drug and no inhibition seen due to drug present in the samples. The percent recoveries remained acceptable mostly between 80-120% regardless of the drug amount present in the samples when compared to the sample results with no drug as a reference. The assay detection sensitivity was maintained at 39 to 63 ng/mL despite drug present at 250 µg/mL, which is higher than the expected Cmax.

5.1 Drug C

Sensitivity and Drug Tolerance Assessment

For Drug C, the assay sensitivity and drug tolerance was compared between the new method and the existing MSD bridging assay with acid dissociation where expected drug tolerance cannot be achieved.

FIGS. 10A-B and 11A-B are summaries of the data for Drug C comparing the bridging assay format with acid dissociation to the PEG and Acid method (PandA).

Figure 10A:
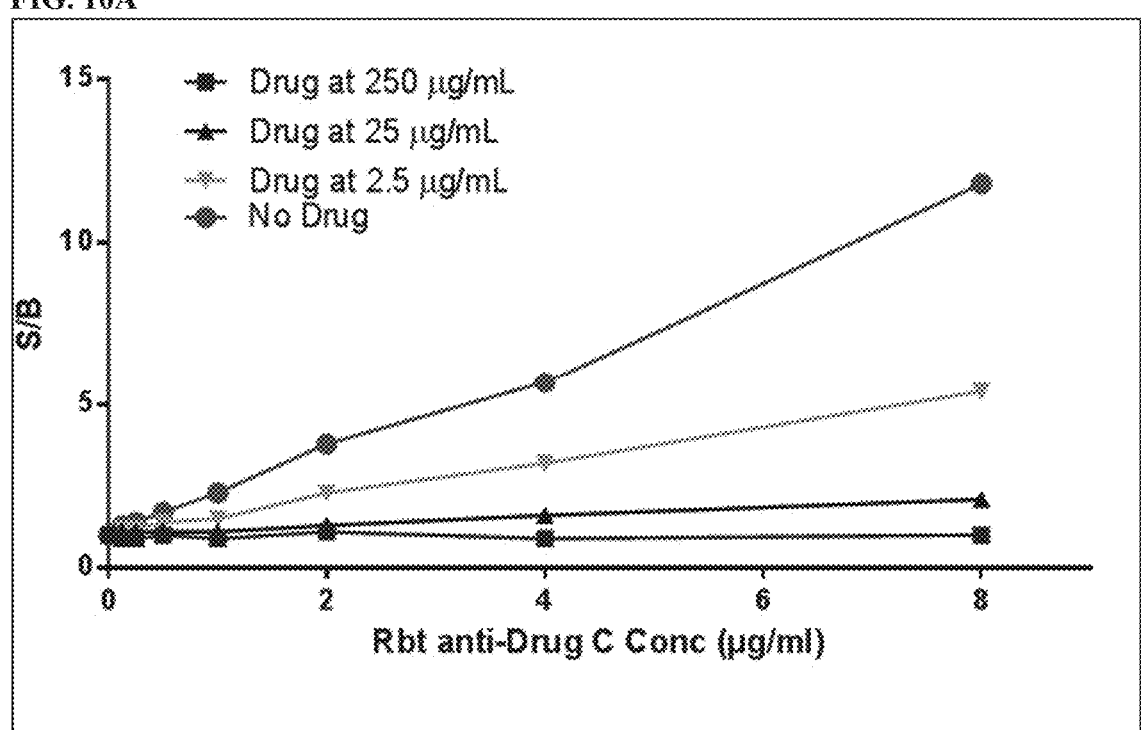
FIGS. 10A and 10B are graphs depicting the results of an example bridging assay format detecting affinity purified rabbit antibody at levels ranging from 8 μg/mL to 125 ng/ml with various concentration of Drug C (0, 2.5, 25 and 250 μg/mL) tested in the MSD bridging assay format with acid dissociation. A. The observed S/B was plotted against the ADA concentration to assess the recovery of the antibody with different levels of drug compared to baseline without drug. B. Percent recovery relative to baseline. S/B: Signal-to-background.
Figure 10B:
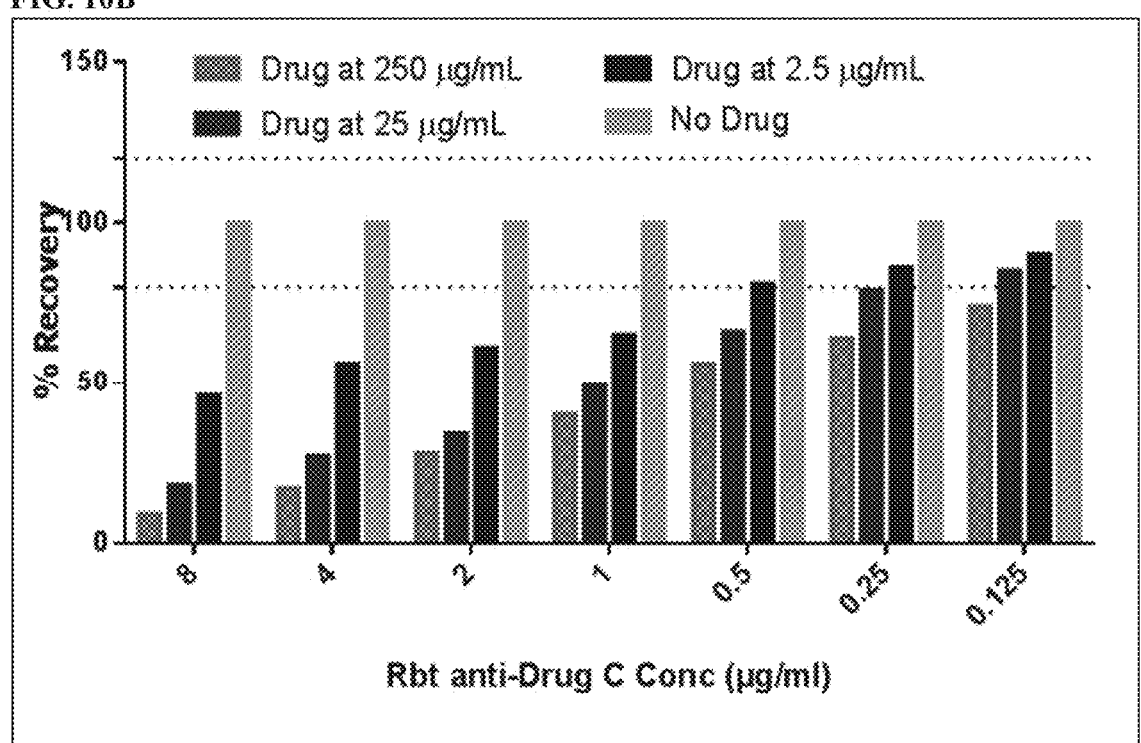

In FIGS. 10A-B, the MSD bridging assay format resulted in an acceptable sensitivity in the absence of drug but inhibition was seen with as little as 2.5 µg/mL of drug despite acid treatment in the bridging immunoassay. The sensitivity of the assay changed from 227 ng/ml to 2788 ng/ml in the presence of 25 µg/mL and antibodies were completely undetectable in the presence of 250 µg/mL of Drug, levels expected in some clinical samples.

Figure 11A:
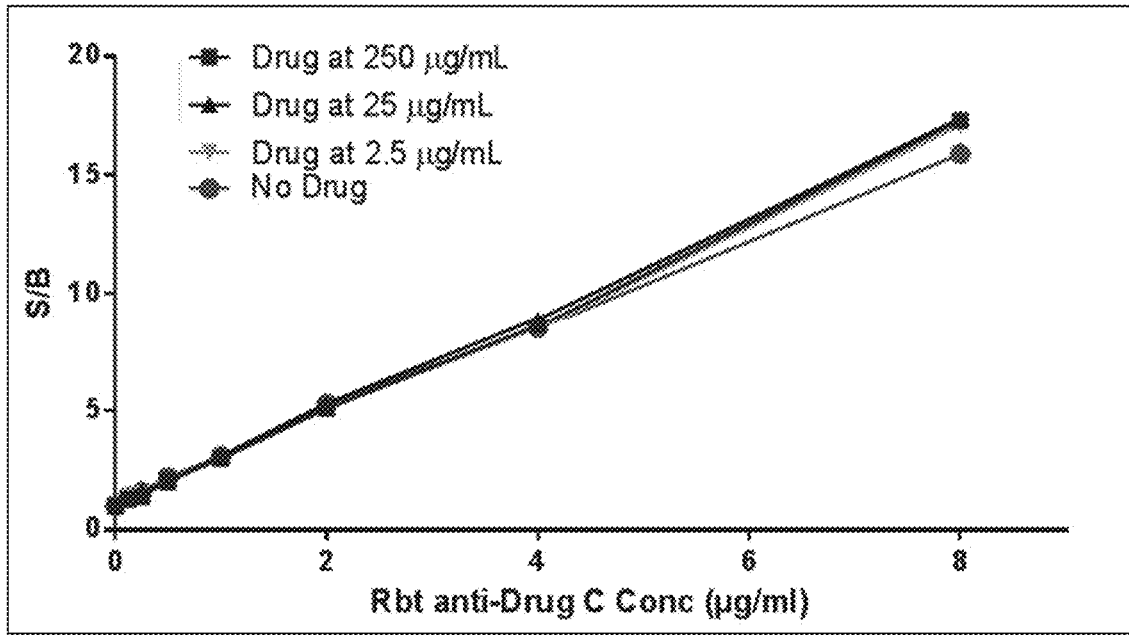
FIGS. 11A and 11B are graphs depicting the results of an example bridging assay format detecting affinity purified rabbit antibody at levels ranging from 8 μg/mL to 125 ng/ml with various concentration of Drug C (0, 2.5, 25 and 250 μg/mL) evaluated in the MSD bridging assay using the PandA assay format. A. The observed S/B was plotted against the ADA concentration to assess the recovery of the antibody with different levels of drug compared to baseline without drug. B. Percent recovery relative to baseline. S/B: Signal-to-background.
Figure 11B:
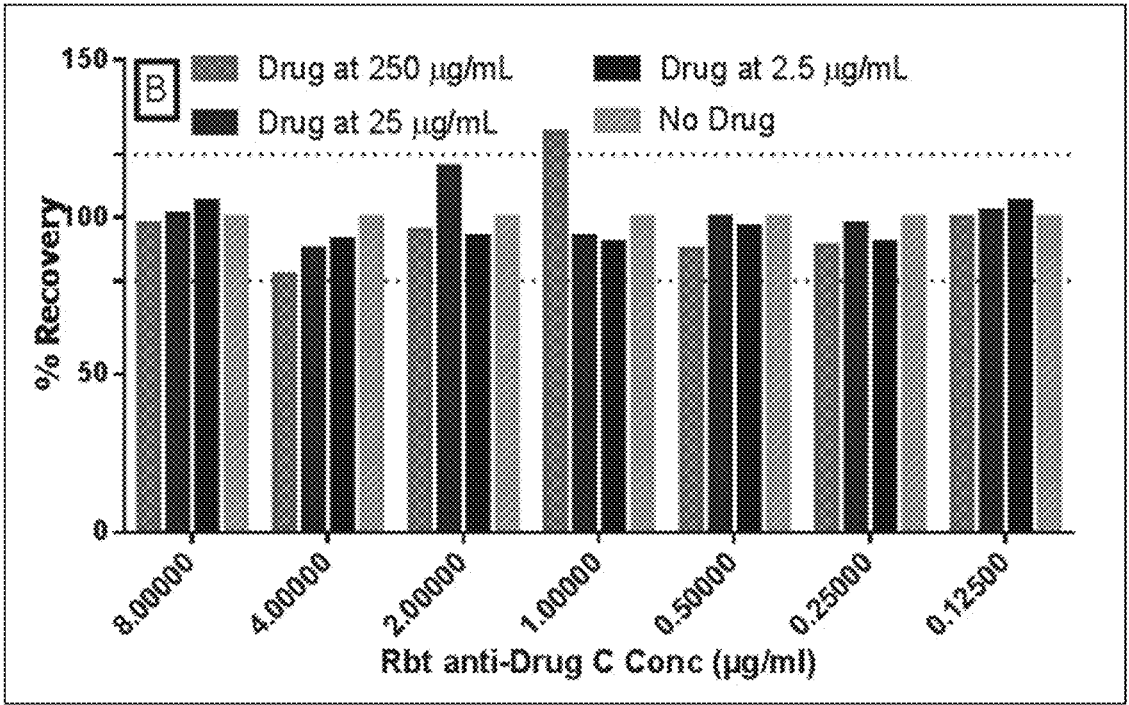

FIGS. 11A-B shows the PandA results to be superior to the bridging immunoassay with acid dissociation where antibody detection was maintained with complete recovery even in the presence of 250 µg/mL of drug. Percent recoveries were observed mostly between 80-120% regardless of the drug amount present in the samples when compared to the sample results with no drug as a reference. The assay detection sensitivity was maintained between 129-175 ng/mL despite drug present at 250 µg/mL, which is higher than what is expected in clinical samples.

The examples above describe case studies for three humanized monoclonal antibodies A-C (an IgG1 and 2 IgG4 drugs).

The three drug specific PandA ADA assays resulted in complete recovery of ADA in samples containing drug levels in excess of those expected in patients, in contrast to the commonly used assay dissociation approach in MSD bridging assays. This breakthrough novel method shows significant improvement over the current approaches. In fact, the drug interference or under detecting of ADA in all three cases were completely eliminated and this assay principle could be used not only for ADA assays but also PK and biomarker (drug target) analysis in the presence of interference factors.

The PandA ADA assay method described herein was shown to be effective at improving both detection and recovery of ADA in samples containing interferent levels in excess of what is clinically relevant. The method also reported consistent antibody titers regardless of the amount of drug present. The method was shown to be superior to the traditional solution based bridging assay with acid dissociation maintaining the ADA detection sensitivity at drug levels in excess of expected clinical Cmax levels and no significant inhibition.

The PandA method can also be applied to PK assays where an ADA or Drug Target is an interferent. Simply, excess antibody (anti-Idiotype) or Target would be added to form complexes and detection will be using a labeled anti-Idiotype that is specific to the drug. In addition, the method can be applicable in drug target biomarker assays with potential drug interference. In summary, the inventors have described a novel application for PEG precipitation of complexes that resolves drug and possibly target interferences in an ADA immunoassay.

Many different methods and platforms have been used with limited success to address circulating drug interference in immunoassays for the detection of ADA. This disclosure a novel method that employs PEG and Acid (PandA) that eliminates drug and possibly target interferences in an ADA immunoassay. The novel method showed complete elimination of drug interference at high drug concentrations and demonstrated while maintaining assay sensitivity in contrast to the traditional solution based MSD bridging assay without or even with acid dissociation. By applying the following assay components, the PandA assay has demonstrated its intended use to sensitively and specifically detect ADA in the presence of drug and/or drug target: addition of excess drug material to form drug/ADA complexes; precipitation using polyethylene glycol to get total ADA; acid dissociation and coating of reconstituted precipitate in an acidic solution on a high bind carbon plate with a large capacity to allow for binding to dissociated ADA; and specific detection of the total ADA levels SULFO-TAG® conjugated drug with an ECL output.

In addition, this method also reported consistent antibody titers regardless of the amount of drug present in the sample showing assay precision. Also reported, the method effectively resolve target interference causing false positive results due to target dimerization in MSD bridging immunoassays with acid dissociation.

In summary, the method is superior to the traditional bridging with acid dissociation method as evidenced by the three proof of principle studies reported above where complete recovery and detection of ADA in samples was achieved with high drug amounts in the samples. This method was successfully validated according to current regulatory expectations and clinical samples tested.

The PandA method described here has shown significant improvement for ADA detection in the presence of excess drug. It has a broad applications based on the principles: (1) saturate free analyte to form all bound analyte in a complex and (2) precipitate the complexes (3) acid dissociate to free analyte without neutralization to reduce analyte re-bound while coating the free analyte under acidic condition onto a large coating surface to immobilize free analyte, and (4) detect free analyte using specific reagent. In the examples above, the inventors have provided three immunogenicity case studies to demonstrate the utility of this novel technology.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing interference in a drug assay due to the presence of an anti-drug antibody (ADA) in a sample, the method comprising:
  contacting the sample with an excess amount of an ADA to saturate free drug and form drug/ADA complexes;
  contacting the drug/ADA complexes with polyethylene glycol (PEG), to thereby form a precipitate comprising drug/ADA complexes;
  contacting the precipitate with a basic solution to dissociate the drug/ADA complexes;
  immobilizing the dissociated drug on a substrate; and
  performing the drug assay, to thereby reduce interference from the ADA.

2. The method of claim 1, wherein the drug assay is selected from the group consisting of a drug quantitation assay, a drug pharmacokinetic (PK) assay, a drug potency assay, and any combinations thereof.

3. The method of claim 1, wherein the drug is selected from the group consisting of an antibody or fragment thereof, a nucleic acid, a peptide, a polypeptide, a peptidomimetic, a carbohydrate, a lipid, an organic small molecule compound, an inorganic small molecule compound, and any combinations thereof.

4. The method of claim 1, further comprising determining the presence or absence of the drug in the sample using an anti-idiotype antibody labeled with a detectable label.

5. The method of claim 1, wherein the drug is modified to exhibit less immunogenicity as compared to the same drug in unmodified form.

6. The method of claim 1, wherein the substrate is selected from the group consisting of a carbon surface, a glass surface, a silica surface, a metal surface, a polymeric material, a surface containing a metallic or a chemical coating, a membrane, micro-beads, a porous polymer matrix, or substrates comprising cellulosic fibers, and any combinations thereof.

7. The method of claim 1, wherein the substrate comprises a high bind carbon plate or a porous carbon surface.

8. The method of claim 1, wherein the substrate comprises a polymeric material.

9. The method of claim 8, wherein the polymeric material is selected from the group consisting of polystyrene, polyvinyl chloride, polypropylene, polyethylene, polyamide, polycarbonate, and any combinations thereof.

10. The method of claim 4, wherein the detectable label comprises a label selected from the group consisting of a radioactive isotope, an enzyme, a fluorescent label, a chemiluminescent label, an electrochemiluminescent label, and a substrate for an enzymatic detection reaction.

11. The method of claim 1, wherein the sample comprises material selected from the group consisting of body fluids, mucus secretions, saliva, blood, plasma, and serum.

12. The method of claim 1, wherein the PEG comprises at least one PEG selected from the group consisting of PEG 1000, PEG 1450, PEG 3000, PEG 6000, PEG 8000, PEG 10000, PEG 14000, PEG 15000, PEG 20000, PEG 25000, PEG 30000, PEG 35000, and PEG 40000.

13. The method of claim 1, wherein the PEG has a molecular weight of between 1,000 and 20,000 Daltons.

14. The method of claim 1, wherein the sample is contacted with PEG at a concentration of between 0.1% and 10.0%, between 3.0% and 6.0%, or between 1.2% and 1.5%.

15. The method of claim 1, wherein the basic solution comprises an organic base, an inorganic base, or a mixture thereof.

16. The method of claim 15, wherein the base is at a concentration of between 0.1 M to 5 M.

17. The method of claim 16, wherein the base is selected from the group consisting of urea, sodium hydroxide, rubidium hydroxide, cesium hydroxide, calcium hydroxide, strontium hydroxide, barium hydroxide, zinc hydroxide, lithium hydroxide, acetone, methylamine, and ammonia, or any combination thereof.

18. The method of claim 1, wherein the drug comprises an antibody or an antigen-binding fragment thereof, and the antibody is a human, humanized or chimeric antibody.

19. The method of claim 1, wherein the drug is selected from the group consisting of an enzyme, a dual affinity antibody, a diabody, a multiple domain biologic, a fusion protein, and a scaffold protein, or any combination thereof.

* * * * *